(12) United States Patent
Goble et al.

(10) Patent No.: US 7,491,737 B2
(45) Date of Patent: Feb. 17, 2009

(54) HETERARYLPIPERIDINE MODULATORS OF CHEMOKINE RECEPTOR ACTIVITY

(75) Inventors: Stephen D. Goble, Edison, NJ (US); Alexander Pasternak, Princeton, NJ (US); Lihu Yang, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 561 days.

(21) Appl. No.: 10/528,304

(22) PCT Filed: Oct. 24, 2003

(86) PCT No.: PCT/US03/34002

§ 371 (c)(1),
(2), (4) Date: Mar. 17, 2005

(87) PCT Pub. No.: WO2004/041777

PCT Pub. Date: May 21, 2004

(65) Prior Publication Data

US 2005/0250781 A1    Nov. 10, 2005

Related U.S. Application Data

(60) Provisional application No. 60/422,447, filed on Oct. 30, 2002.

(51) Int. Cl.
   A61K 31/454    (2006.01)
   A61K 31/4545   (2006.01)

(52) U.S. Cl. .............. 514/326; 546/207; 546/208; 546/209; 546/210; 546/211

(58) Field of Classification Search .............. 514/304, 514/326
See application file for complete search history.

(56) References Cited

U.S. PATENT DOCUMENTS

| | | | |
|---|---|---|---|
| 5,843,966 A | | 12/1998 | Armou et al. |
| 6,140,338 A | * | 10/2000 | Naya et al. ............... 514/299 |
| 6,248,755 B1 | * | 6/2001 | Chapman et al. ........... 514/320 |
| 6,498,161 B1 | * | 12/2002 | Caldwell et al. ....... 514/252.03 |
| 6,531,484 B2 | * | 3/2003 | Willoughby et al. ........ 514/304 |
| 2005/0250814 A1 | | 11/2005 | Zhou et al. |
| 2005/0261325 A1 | | 11/2005 | Butora et al. |
| 2006/0116421 A1 | | 6/2006 | Butora et al. |
| 2006/0173013 A1 | | 8/2006 | Zhou et al. |

FOREIGN PATENT DOCUMENTS

| | | |
|---|---|---|
| WO | WO 02/13824 | 1/2002 |
| WO | WO/0213824 * | 2/2002 |
| WO | WO 2004/110376 | 12/2004 |

OTHER PUBLICATIONS

Xia et. al. "Synthesis and biological evaluation of phenyl piperidine derivatives as CCR2 antagonists" Bioorganic & Medicinal Chemistry Letters 2007; 17, 5964-5968.*
Anthony B. Pinkerton "Diaryl substituted pyrazoles as potent CCR2 receptor antagonists" Bioorganic & Medicinal Chemistry Letters 2007, 17, 807-813.*
Yang et. al. "Discovery of 3,5-bis(trifluoromethyl)benzyl L-arylglycinamide based potent CCR2 antagonists" Bioorganic & Medicinal Chemistry Letters 2006, 16, 3735-3739.*
Pozharskii et. al. Heterocycles in Life and Society Wiley, 1997, pp. 1-6.*

* cited by examiner

*Primary Examiner*—Rita J Desai
*Assistant Examiner*—David K O'Dell
(74) *Attorney, Agent, or Firm*—James L. McGinnis; Mark Daniel

(57) ABSTRACT

The present invention is directed to compounds of the formula (I): (wherein $R_1$, $R_2$, $R_3$, $R_4$, $R_5$, $R_6$, $R_{10}$ and n are defined herein) which are useful as modulators of chemokine receptor activity. In particular, these compounds are useful as modulators of the chemokine receptor CCR-2.

8 Claims, No Drawings

HETERARYLPIPERIDINE MODULATORS OF CHEMOKINE RECEPTOR ACTIVITY

RELATED APPLICATION DATA

This is a National filing under 35 USC 371 of PCT/US2003/34002, Oct. 24, 2003, which claims priority from USSN 60/422,447, filed Oct. 30, 2002.

BACKGROUND OF THE INVENTION

The chemokines are a family of small (70-120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, Cytokine, 3, 165-183 (1991) and Murphy, Rev. Immun. 12, 593-633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The α-chemokines, such as interleukin-8 (IL 8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, monocytes, T-cells, eosinophils and basophils (Deng, et al., Nature, 381, 661-666 (1996)).

The chemokines are secreted by a wide variety of cell types and bind to specific G-protein coupled receptors (GPCRs) (reviewed in Horuk, Trends Pharm. Sci., 15, 159-165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., J. Biol. Chem., 270, 22123-22128 (1995); Beote, et al, Cell, 72, 415-425 (1993)); CCR-2A and CCR-2B (or "CKR-2A"/"CKR-2A" or "CC-CKR-2A"/"CC-CKR-2A") [MCP-1, MCP-2, MCP-3, MCP4]; CCR-3 (or "CKR-3" or "CC-CKR-3") [Eotaxin, Eotaxin 2, RANTES, MCP-2, MCP-3] (Rollins, et al., Blood, 90, 908-928 (1997)); CCR-4 (or "CKR-4" or "CC-CKR-4") [MIP-1α, RANTES, MCP-1] (Rollins, et al., Blood, 90, 908-928 (1997)); CCR-5 (or "CKR-5" or "CC-CKR-5") [MIP-1α, RANTES, MIP-1β] (Sanson, et al., Biochemistry. 35, 3362-3367 (1996)); and the Duffy blood-group antigen [RANTES, MCP-1] (Chaudhun, et al., J. Biol. Chem., 269, 7835-7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., Arthritis & Rheumatism, 42, 989-992 (1999)). A review of the role of eosinophils in allergic inflammation is provided by Kita, H., et al., J. Exp. Med. 183, 2421-2426 (1996). A general review of the role of chemokines in allergic inflammation is provided by Lustger, A. D., New England J. Med., 338(7), 426445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and Listeria monocytogenes infection (Lu et al., J. Exp. Med. 187:601-608 (1998); Kurihara et al. J. Exp. Med. 186: 1757-1762 (1997); Boring et al. J. Clin. Invest. 100:2552-2561 (1997); Kuziel et al. Proc. Natl. Acad. Sci. 94:12053-12058 (1997)). Furthermore, these animals show reduced monocyte infiltration into granulomatous lesions induced by the injection of schistosomal or mycobacterial antigens (Boring et al. J. Clin. Invest. 100:2552-2561 (1997); Warmington et al. Am J. Path. 154:1407-1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1 −/− or CCR2 −/− mice backcrossed to APO-E −/−, LDL-R −/− or Apo B transgenic mice maintained on high fat diets (Boring et al. Nature 394: 894-897 (1998); Gosling et al. J. Clin. Invest. 103:773-778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of the formula I:

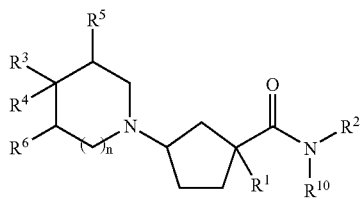

I wherein:
$R^1$ is selected from:
  hydrogen,
  —$C_{0-6}$alkyl-Y-($C_{1-6}$alkyl)-, and
  —($C_{0-6}$alkyl)-Y-($C_{0-6}$alkyl)($C_{3-7}$cycloalkyl)-($C_{0-6}$alkyl),
    where Y is selected from:
      a single bond, —O—, —S—, —SO—, —$SO_2$—, and —$NR^{10}$—,
    and where the alkyl and the cycloalkyl are unsubstituted or substituted with 1-7 substituents where the substituents are independently selected from:
      (a) halo,
      (b) hydroxy,
      (c) —O—$C_{1-3}$alkyl, and
      (d) trifluoromethyl,
      (e) $C_{1-3}$alkyl,
      (f) —O—$C_{1-3}$alkyl,
      (g) —$CO_2R^9$, wherein $R^9$ is independently selected from: hydrogen, $C_{1-6}$ alkyl, $C_{5-6}$ cycloalkyl, benzyl or phenyl, which is unsubstituted or substituted with 1-3 substituents where the substituents are independently selected from: halo, $C_{1-3}$alkyl, $C_{1-3}$alkoxy and trifluoromethyl,
      (h) —CN,
      (i) heterocycle,
      (j) —$NR^9R^{10}$,
      (k) —$NR^9COR^{10}$,
      (l) —$NR^9SO_2R^{10}$, and
      (m) —$CONR^9R^{10}$;
$R^2$ is selected from:
  ($C_{0-6}$alkyl)-phenyl and ($C_{0-6}$alkyl)-heterocycle,
    where the alkyl is unsubstituted or substituted with 1-7 substituents where the substituents are independently selected from:
      (a) halo,
      (b) hydroxy,
      (c) —O—$C_{1-3}$alkyl,
      (d) trifluoromethyl, and
      (e) —$C_{1-3}$alkyl,
    and where the phenyl and the heterocycle is unsubstituted or substituted with 1-5 substituents where the substituents are independently selected from:
      (a) halo,
      (b) trifluoromethyl,
      (c) trifluoromethoxy,
      (d) hydroxy,
      (e) $C_{1-6}$alkyl,
      (f) $C_{3-7}$cycloalkyl,
      (g) —O—$C_i$alkyl,
      (h) —O—$C_{3-7}$cycloalkyl,
      (i) —$SCF_3$,
      (j) —S—$C_1$-alkyl,
      (k) —$SO_2$—$C_{1-6}$alkyl,
      (l) phenyl,
      (m) heterocycle,
      (n) —$CO_2R^9$,
      (o) —CN,
      (p) —$NR^9R^{10}$,
      (q) —$NR^9$—$SO_2$—$R^{10}$,
      (r) —$SO_2$—$NR^9R^{10}$, and
      (s) —$CONR^9R^{10}$;
$R^3$ is selected from:
  ($C_{0-6}$alkyl)-heterocycle,
    where the alkyl is unsubstituted or substituted with 1-5 substituents where the substituents are independently selected from:
      (a) halo,
      (b) hydroxy,
      (c) —O—$C_{1-3}$alkyl, and
      (d) trifluoromethyl, and where the heterocycle is unsubstituted or substituted with 1-5 substituents where the substituents are independently selected from:
      (a) halo,
      (b) trifluoromethyl,
      (c) hydroxy,
      (d) $C_{1-3}$alkyl,
      (e) —O—$C_{1-3}$alkyl,
      (f) —$CO_2R^9$,
      (g) —CN,
      (h) —$NR^9R^{10}$, and
      (i) —$CONR^9R^{10}$;
$R^4$ is selected from:
  (a) hydrogen,
  (b) hydroxy,
  (c) $C_{1-6}$alkyl,
  (d) $C_{1-6}$alkyl-hydroxy,
  (e) —O—$C_{1-3}$alkyl,
  (f) —$CO_2R^9$,
  (g) —$CONR^9R^{10}$, and
  (h) —CN;
$R^5$ and $R^6$ are independently selected from:
  (a) hydrogen,
  (b) hydroxy,
  (c) $C_{1-6}$alkyl,
  (d) $C_{1-6}$alkyl-hydroxy,
  (e) —O—$C_{1-3}$alkyl,
  (f) oxo, and
  (g) halo;
$R^{10}$ is independently selected from:
  hydrogen, $C_{1-6}$ alkyl, benzyl, phenyl, and $C_{1-6}$ alkyl-$C_{3-6}$ cycloalkyl, which is unsubstituted or substituted with 1-3 substituents where the substituents are independently selected from: halo, $C_{1-3}$alkyl, $C_{1-3}$alkoxy and trifluoromethyl;
n is an integer which is 0 or 1; and pharmaceutically acceptable salts thereof and individual diastereomers thereof.

In the present invention it is preferred that $R^1$ is selected from:
—$C_{1-6}$alkyl, —$C_{0-6}$alkyl-O—$C_{1-6}$alkyl-, —$C_{0-6}$alkyl-S—$C_{1-6}$alkyl-, and
—($C_{0-6}$alkyl)-($C_{3-7}$cycloalkyl)($C_{0-6}$alkyl),
  where the alkyl and the cycloalkyl are unsubstituted or substituted with 1-7 substituents where the substituents are independently selected from:
    (a) halo,
    (b) hydroxy,
    (c) —O—$C_{1-3}$alkyl,
    (d) trifluoromethyl,
    (f) $C_{1-3}$alkyl,
    (g) —O—$C_{1-3}$alkyl,
    (h) —$CO_2R^9$, wherein $R^9$ is independently selected from: hydrogen, $C_{1-6}$alkyl, $C_{5-6}$ cycloalkyl, benzyl or phenyl, which is unsubstituted or substituted with 1-3 substituents where the substituents are independently selected from: halo, $C_{1-3}$alkyl, $C_{1-3}$alkoxy and trifluoromethyl,
    (i) —CN,
    (j) —$NR^9R^{10}$, and
    (k) —$CONR^9R^{10}$.

In the present invention it is more preferred that $R^1$ is selected from:
(1) —$C_{1-6}$alkyl, which is unsubstituted or substituted with 1-6 substituents where the substituents are independently selected from:
  (a) halo,
  (b) hydroxy,
  (c) —O—$C_{1-3}$alkyl, and
  (d) trifluoromethyl,
(2) —$C_{0-6}$alkyl-O—$C_{1-6}$alkyl-, which is substituted or substituted with 1-6 substituents where the substituents are independently selected from:
  (a) halo, and
  (b) trifluoromethyl,
(3) —$C_{0-6}$alkyl-S—$C_{1-6}$alkyl-, which is unsubstituted or substituted with 1-6 substituents where the substituents are independently selected from:
  (a) halo, and
  (b) trifluoromethyl,
(4) —($C_{3-5}$cycloalkyl)-($C_{0-6}$alkyl), which is unsubstituted or substituted with 1-7 substituents where the substituents are independently selected from:
  (a) halo,
  (b) hydroxy,
  (c) —O—$C_{1-3}$alkyl, and
  (d) trifluoromethyl.

In the present invention it is even more preferred that $R^1$ is selected from:
(1) —$CH_3$,
(2) —$CH_2CH_3$,
(3) —$CH(CH_3)_2$,
(4) —$CH_2CH_2CH_3$,
(5) —$CH_2CH(CH_3)_2$,
(6) -cyclopropyl,
(7) -cyclobutyl,
(8) -cyclopentyl,
(9) —$CH_2$-cyclopropyl,
(10) —$CH_2$-cyclobutyl,
(11) —$CH_2$-cyclopentyl,
(12) —$CH_2OH$,
(13) —$C(CH_3)_2(OH)$,
(14) —$C(CH_2OH)(CH_3)_2$,
(15) —(OH)cyclobutyl,
(16) —(OH)cyclopentyl,
(17) —$C(CH_3)_2(NHCOCH_3)$,
(18) —$C(CO_2H)(CH_3)_2$,
(19) —O—$CH_3$,
(20) —O-cyclopentyl,
(21) —O—$CH(CH_3)_2$,
(22) —S—$CH_3$,
(23) —S—$CF_3$,
(24) —$SO_2$—$CH_3$,
(25) —S—$CH(CH_3)_2$,
(26) —$SO_2$—$CH(CH_3)_2$, and
(27) —NH—$SO_2$—$CH_3$.

In the present invention it is preferred that $R^2$ is selected from:
—($C_{0-4}$alkyl)-phenyl and —($C_{0-4}$alkyl)-heterocycle,
  where heterocycle is selected from:
    furanyl, imidazolyl, oxadiazolyl, oxazolyl, pyrazolyl, pyrazinyl, pyridyl, pyridazinyl, pyrimidyl, pyrrolyl, thiadiazolyl, thiazolyl, thienyl, and triazolyl, and N-oxides thereof,
  where the alkyl is unsubstituted or substituted with 1-7 substituents where the substituents are independently selected from:
    (a) halo,
    (b) hydroxy,
    (c) —O—$C_{1-3}$alkyl, and
    (d) trifluoromethyl,
  and where the phenyl or heterocycle is unsubstituted or substituted with 1-5 substituents where the substituents are independently selected from:
    (a) halo,
    (b) trifluoromethyl,
    (c) trifluoromethoxy,
    (d) hydroxy,
    (e) $C_{1-3}$alkyl,
    (f) —O—$C_{1-3}$alkyl,
    (g) —$CO_2R^9$,
    (h) —S—$C_{1-3}$alkyl,
    (i) —$SO_2$—$C_{1-3}$alkyl,
    (j) —$SCF_3$,
    (k) —$CO_2R^9$,
    (l) —$NR^9R^{10}$,
    (m) —$NR^9$—$SO_2$—$R^{10}$,
    (n) —$SO_2$—$NR^9R^{10}$, and
    (o) —$CONR^9R^{10}$.

In the present invention it is more preferred that $R^2$ is selected from:
—($C_{0-4}$alkyl)-phenyl and —($C_{0-4}$alkyl)-heterocycle,
  where heterocycle is selected from: pyridyl, pyridazinyl, and N-oxides thereof,
  where the alkyl is unsubstituted or substituted with 1-7 substituents where the substituents are independently selected from:
    (a) halo,
    (b) hydroxy,
    (c) —O—$C_{1-3}$alkyl, and
    (d) trifluoromethyl,
  and where the phenyl or heterocycle is unsubstituted or substituted with 1-3 substituents where the substituents are independently selected from:
    (a) halo,
    (b) trifluoromethyl,
    (c) trifluoromethoxy,
    (d) hydroxy,
    (e) $C_{1-3}$alkyl,
    (f) —O—$C_{1-3}$alkyl,
    (g) —$CO_2$—$C_{1-3}$alkyl,
    (h) —$CO_2H$, (i) —S—$C_{1-3}$alkyl,
(j) —$SO_2$-$C_{1-3}$alkyl,
(k) —$SCF_3$,
(l) —$NH_2$,
(m) —NH—$SO_2$-$C_{1-3}$alkyl, and
(n) —$SO_2$—$NH_2$.

In the present invention it is even more preferred that $R^2$ is selected from:
—$CH_2$-phenyl and —$CH_2$-heterocycle,
where heterocycle is selected from: pyridyl, pyridazinyl, and N-oxides thereof,
and where the phenyl or heterocycle is unsubstituted or substituted with 1-3 substituents where the substituents are independently selected from:
(a) halo,
(b) trifluoromethyl,
(c) trifluoromethoxy,
(d) hydroxy,
(e) $C_{1-3}$alkyl,
(f) —O—$C_{1-3}$alkyl,
(g) —$CO_2$—$C_{1-3}$alkyl,
(h) —$CO_2H$,
(i) —S—$C_{1-3}$alkyl,
(j) —$SO_2$—$C_{1-3}$alkyl,
(k) —$SCF_3$,
(l) —$NH_2$,
(m) —NH—$SO_2$—$C_{1-3}$alkyl, and
(n) —$SO_2$—$NH_2$.

In the present invention it is still more preferred that $R^2$ is selected from:
(1) —$CH_2$-(phenyl),
(2) —$CH_2$-(4-bromophenyl),
(3) —$CH_2$-(3chlorophenyl),
(4) —$CH_2$-(3,5-difluorophenyl),
(5) —$CH_2$-((2-trifluoromethyl)phenyl),
(6) —$CH_2$-((3-trifluoromethyl)phenyl),
(7) —$CH_2$-(4trifluoromethyl)phenyl),
(8) —$CH_2$-((3-trifluoromethoxy)phenyl),
(9) —$CH_2$-((3-trifluoromethylthio)phenyl),
(10) —$CH_2$-((3-trifluoromethoxy-5-thiomethyl)phenyl),
(11) —$CH_2$-((3-trifluoromethoxy-5-methoxy)phenyl),
(12) —$CH_2$-((3-trifluoromethoxy-5-methanesulfonyl)phenyl),
(13) —$CH_2$-((3-trifluoromethoxy-5-amino)phenyl),
(14) —$CH_2$-((3-trifluoromethoxy-5-aminomethanesulfonyl) phenyl),
(15) —$CH_2$-((3-trifluoromethoxy-5-sulfonylamino)phenyl),
(16) —$CH_2$-((3,5-bis-trifluoromethyl)phenyl),
(17) —$CH_2$-((3-fluoro-5-trifluoromethyl)phenyl),
(18) —$CH(CH_3)$-((3,5-bis-trifluoromethyl)phenyl),
(19) —$C(CH_3)_2$-((3,5-bis-trifluoromethyl)phenyl),
(20) —$CH_2$-(4-(2-trifluoromethyl)pyridyl),
(21) —$CH_2$-(5-(3-trifluoromethyl)pyridyl),
(22) —$CH_2$-(5-(3-trifluoromethyl)pyridazinyl),
(23) —$CH_2$-(4-(2-trifluoromethyl)pyridyl-N-oxide), and
(24) —$CH_2$-(5-(3-trifluoromethyl)pyridyl-N-oxide).

In the present invention it is preferred that $R^3$ is heterocycle,
where the heterocycle is unsubstituted or substituted with 1-5 substituents where the substituents are independently selected from:
(a) halo,
(b) trifluoromethyl,
(c) hydroxy,
(d) $C_{1-3}$alkyl,
(e) —O—$C_{1-3}$alkyl,
(f) —$CO_2R^9$, (g) —CN,
(h) —$NR^9R^{10}$, and
(i) —$CONR^9R^{10}$.

In the present invention it is preferred that $R^3$ is heterocycle, where the heterocycle is selected from: imidazole, pyrimidyl, triazole or tetrazole, and
where the heterocycle is unsubstituted or substituted with 1-5 substituents where the substituents are independently selected from:
(a) halo,
(b) trifluoromethyl,
(c) hydroxy,
(d) $C_{1-3}$alkyl,
(e) —O—$C_{1-3}$alkyl,
(f) —$CO_2R^9$,
(g) —CN,
(h) —$NR^9R^{10}$, and
(i) —$CONR^9R^{10}$.

In the present invention it is more preferred that $R^3$ is heterocycle,
where the heterocycle is unsubstituted or substituted with 1-3 substituents where the substituents are independently selected from:
(a) halo,
(c) hydroxy,
(d) $C_{1-3}$alkyl,
(e) —O—$C_{1-3}$alkyl, and
(f) —$CO_2R^9$.

In the present invention it is still more preferred that $R^3$ is selected from: imidazole, pyrimidyl, triazole or tetrazole.

In the present invention it is preferred that $R^3$ is selected from:

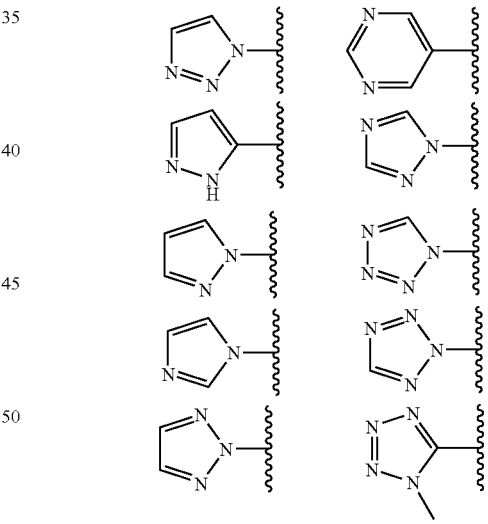

In the present invention it is preferred that $R^4$ is selected from:
(a) hydrogen,
(b) hydroxy,
(c) —$CO_2H$,
(d) —$CO_2C_{1-6}$alkyl,
(e) —CN.

In the present invention it is preferred that $R^4$ is hydrogen.
In the present invention it is preferred that $R^5$ and $R^6$ are independently selected from:
(a) hydrogen,
(b) hydroxy, (c) —CH₃,
(d) —O—CH₃, and
(e) oxo.

In the present invention it is more preferred that R⁵ is independently selected from:
(a) hydrogen,
(b) —CH₃, and
(c) —O—CH₃.

The compounds of the instant invention have at least two asymmetric centers at the 1- and 3-positions of the cyclopentyl ring. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The absolute configurations of the more preferred compounds of this invention are of the orientation where the piperidinyl substituent and the X substituent are cis, i.e. as depicted:

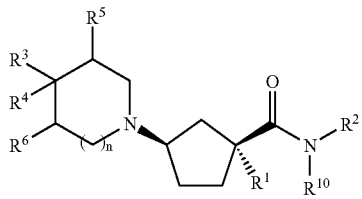

The absolute configurations of the most preferred compounds of this invention are those of the orientation as depicted:

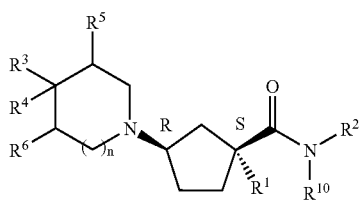

wherein the piperidinyl substituent is designated as being of the "R" absolute configuration and the X substituent is designated as being of the "S" absolute configuration (although the designation for the X substituent may be specified as "R" if the priority for assignment of the groups at that position differs).

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$alkyl is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. Likewise, $C_0$, as in $C_0$alkyl is defined to identify the presence of a direct covalent bond. The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media such as ether, ethyl acetate, ethanol, isopropanol, or acetonitrile are preferred. Suitable salts are found, e.g. in Remington's. Pharmaceutical Sciences, 17th ed., Mack Publishing Company, Easton, Pa., 1985, p. 1418.

Exemplifying the invention is the use of the compounds disclosed in the Examples and herein.

Specific compounds within the present invention include a compound which selected from the group consisting of: the title compounds of the Examples; and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851-856 (1993) which may be readily adapted for measurement of CCR-2 binding.

Receptor affinity in a CCR-2 binding assay was determined by measuring inhibition of 125I-MCP-1 to the endogenous CCR-2 receptor on various cell types including monocytes, THP-1 cells, or after heterologous expression of the cloned receptor in eukaryotic cells. The cells were suspended in binding buffer (50 mM Hepes, pH 7.2, 5 mM $MgCl_2$, 1 mM $CaCl_2$, and 0.50% BSA) with and added to test compound or DMSO and $^{125}$I-MCP-1 at room temperature for 1 h to allow binding. The cells were then collected on GFB filters, washed with 25 mM Hepes buffer containing 500 mM NaCl and cell bound $^{125}$I-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuraminidase-treated sheep erythrocytes. Once isolated, the cells were washed with HBSS containing 0.1 mg/ml BSA and suspended at $1\times10^7$ cells/ml. Cells were fluorescently labeled in the dark with 2 µM Calcien-AM (Molecular Probes), for 30 min at 37° C. Labeled cells were washed twice and suspended at $5\times10^6$ cells/ml in RPMI 1640 with L-glutamine (without phenol red) containing 0.1 mg/ml BSA. MCP-1 (Peprotech) at 10 ng/ml diluted in same medium or medium alone were added to the bottom wells (27 µl). Monocytes (150,000 cells) were added to the topside of the filter (30 µl) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant In particular, the compounds of the following examples had activity in binding to the CCR-2 receptor in the aforementioned assays, generally with an $IC_{50}$ of less than about 1 µM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, compounds which inhibit or promote chemokine receptor function would be useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In a preferred embodiment, the disease or condition is one in which the actions of lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with modulators of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (*Trichuriasis, Enterobiasis, Ascariasis*, Hookworm, *Strongyloidiasis, Trichinosis, filariasis*), trematodes (flukes) (*Schistosomiasis, Clonorchiasis*), cestodes (tape worms) (*Echinococcosis, Taeniasis saginata, Cysticercosis*), visceral worms, visceral larva migraines (e.g., *Toxocara*), eosinophilic gastroenteritis (e.g., *Anisaki* sp., *Phocanema* sp.), and cutaneous larva migraines (*Ancylostona braziliense, Ancylostoma caninum*). In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in the prevention and treatment of a wide variety of inflammatory and immunoregulatory disorders and diseases, allergic conditions, atopic conditions, as well as autoimmune pathologies. In a specific embodiment, the present invention is directed to the use of the subject compounds for the prevention or treatment of autoimmune diseases, such as rheumatoid arthritis or psoriatic arthritis.

In another aspect, the instant invention may be used to evaluate putative specific agonists or antagonists of chemokine receptors, including CCR-2. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in the prevention or treatment of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

As used herein, the term "treatment" refers both to the treatment and to the prevention or prophylactic therapy of the aforementioned conditions.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, embrel, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever, a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxyephedrine; an antiitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alrinoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PD-IV); (i) other antagonists of the chemokine receptors, especially CCR-1, CCR-2, CCR-3, CXCR-3 and CCR-5; (j) cholesterol lowering agents such as HMG-CoA reductase inhibitors (lovastatin, simvastatin and pravastatin, fluvastatin, atorvastatin, rosuvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) antidiabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos.

4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservative. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made by known procedures or as illustrated.

Several methods for preparing the compounds of this invention are illustrated in the following Schemes and Examples. Starting materials are made by known procedures or as illustrated.

SCHEME 1

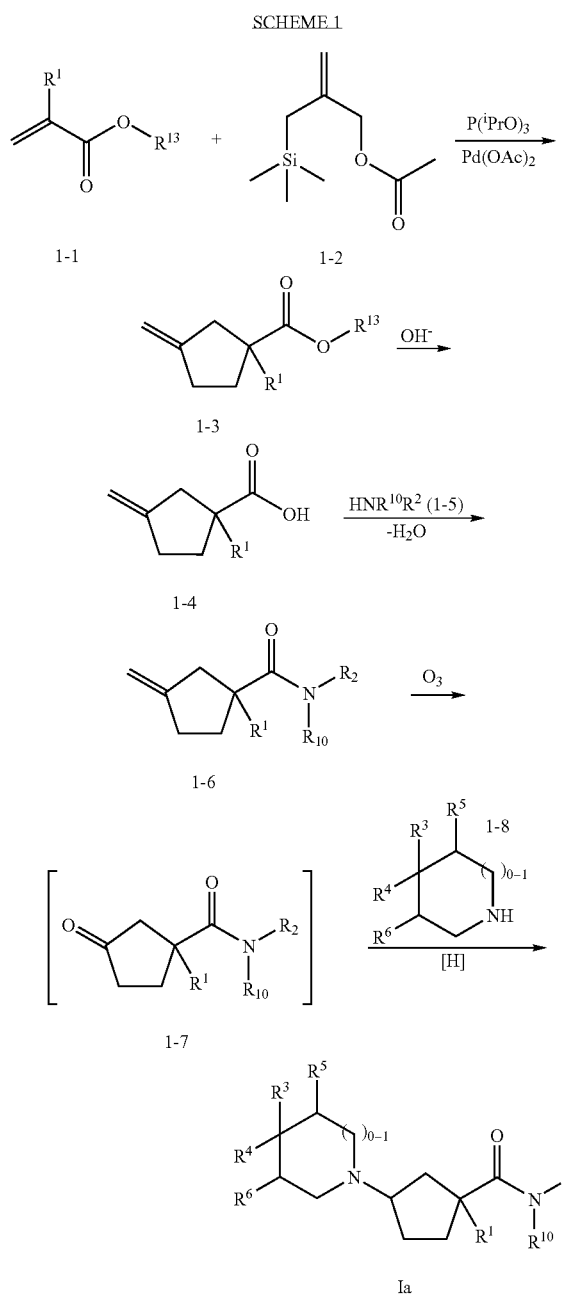

The preparation of compounds within the scope of the instant invention which bear a 1,1,3-trisubstituted cyclopentane framework is detailed in Scheme 1. Treatment of an acrylate such as 1-1 with commercially available 2-[(trimethylsilyl)-methyl]-2-propen-1-yl acetate (1-2) in the presence of a substoichiometric amount of palladium acetate and triisopropylphosphite (or other Pd⁰ equivalent) in TBF, according to a known procedure (Trost, B. M., Chan, D. M. T. *J. Am. Chem. Soc.* 1983,105, 2315) affords the 1-substituted-2-methylene carboxylate 1-3. $R^{13}$ represents an alkyl such as methyl, ethyl, tert-butyl or benzyl which serves as a protecting group (Greene, T; Wuts, P. G. M. *Protective Groups in Organic Synthesis*, John Wiley & Sons, Inc., New York, N.Y. 1991). Conversion of ester 1-3 to the carboxylic acid 1-4 can be achieved by a number of conditions depending on the nature of the ester. For example, methyl or ethyl esters can be readily saponified with sodium hydroxide, or lithium hydroxide; tert-butyl ester can be removed by treatment with TFA. Coupling of the acid 1-4 with amine 1-5 to give amide 1-6 can be accomplished by the standard amide bond formation conditions using a coupling reagent such as DCC, EDC and a catalyst such as DMAP, HOBT or HOAT. Oxidation of the olefin 1-6 to the ketone 1-7 can be carried out under numerous conditions, such as with ozone followed by treatment with methyl sulfide or triphenylphosphine, with osmium tetroxide and sodium periodate (see March J. "Advanced Organic Chemistry", 4th ed., John Wiley & Sons, New York, pp. 1167-1171 (1992)). Reductive amination with cyclic amine 1-8 in the presence of a borohydride such as sodium triacetoxyborohydride or sodium cyanoborohydride then provides the compound of formula Ia.

Alternatively, compounds of formula Ia may be prepared in one pot by reductive amination of the ozonide without converting it to the ketone. Substitutions at position 1 and 3 on the cyclopentane ring created four isomers. These isomers can be separated by chromatography using normal phase, reverse phase, or chiral columns depending on the nature of the separations.

SCHEME 1A

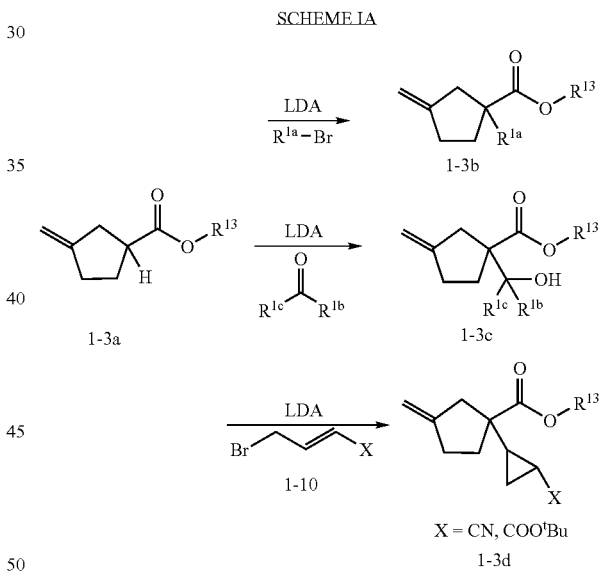

The preparation of olefin-esters 1-3 as intermediates can also be achieved through the commercially available methyl 3-methylene-1-methyl-cyclopentane carboxylate, as depicted in Scheme 1A. The methyl ester can be converted to other esters depending on need. Direct alkylation of 1-3a to give 1-3b can be achieved by an alkyl halide such as a bromide 1-8 and a strong base such as sodium, lithium or potassium hexamethyldisilazide, lithium diisopropylamide, and the like. Aldol reduction of an enolate of 1-3a with a ketone or aldehyde 1-9, as well as Michael additions with bromocrotonates 1-10 followed by ring closure yield the aldol 1-3c and cyclopropylsubstituted intermediates 1-3d, respectively. These compounds can be then converted to the compound of formula Ia according to Scheme 1.

SCHEME 2

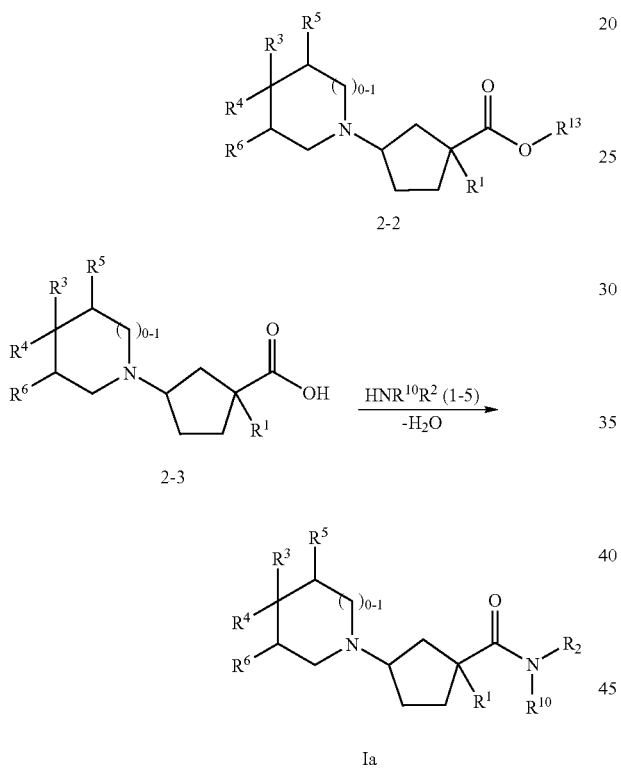

As depicted in Scheme 2, the C1-substituted allyl 3-methylene-cyclopentanecarboxylate (intermediate 1-3) could be converted to intermediate ketone 2-1 by ozonolysis of the olefin group in position 3 of the cyclopentane ring, followed by reduction of the formed ozonide, as described for intermediate 1-7. The ketone 2-1 could be in turn reductively aminated with amine 1-5 to form the amino ester 2-2 under a variety of conditions, including sodium triacetoxyborohydride or sodium cyanoborohydride. The intermediate ozonide could be also successfully subjected to above mentioned conditions of reductive amination with amines 1-5 to form the esters 2-2 directly in a one pot operation, similarly to that described above.

The intermediate esters 2-2, formed in the above mentioned transformations represent in general a mixture of 1,3-cis- and 1,3-trans-diastereoisomers, which could be separated into respective diastereoisomeric pairs using column chromatography. A similar diastereoisomeric separation could be also accomplished later, after the esters 2-2 were hydrolytically cleaved to yield the respective acids 2-3. This hydrolysis was readily accomplished under usual conditions, including lithium, sodium or potassium hydroxide, at ambient to elevated temperatures, depending on the nature of the ester group and substituent $R^1$. These diastereoisomers could be separated by crystallization from a variety of solvents, taking advantage of the finding, that the cis-diastereoisomeric acids are less soluble, when compared to their trans-epimers.

The compounds of formula Ia are then formed from the acids 2-3 and amines 1-5 under standard amide-bond forming reaction conditions, including carbodiimide reagents, such as DCC, EDC and catalysts such as DMAP, HOAT or HOBT.

SCHEME 3

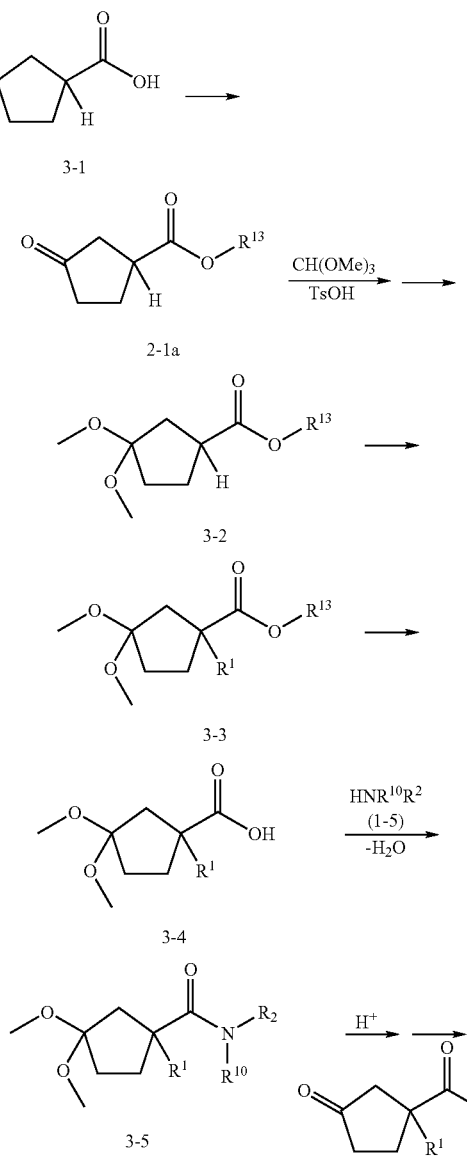

Preparation of the ketone 1-7 for use as an intermediate in the synthesis of compounds in the instant invention can be alternatively achieved as shown in Scheme 3. The known 3-oxocyclopentane carboxylic acid 3-1 (Stetter & Kuhlmann, *Liebigs Ann. Chem.* 1979, 944-949) is converted to ester 2-1a through conventional esterification conditions. The tert-Butyl ester was conveniently prepared by reaction of isobutylene, generated from tert-butyl alcohol with an appropriate acid in situ (Wright, S. W., Hageman, D. L., Wright, A. S., McClure, L. D. *Tetrahedron Lett.*, 1997, 38, 7345) or using N,N'-diisopropyl-O-tert-Butyl-iso-urea (Burk, R. M., Berger, G. D., Bugianesi, R. L., Girotra, N. N., Parsons, W. H., Ponpipom, M. M. *Tetrahedron Lett.*, 1993, 34, 975) as a convenient reagent. Treatment of 2-1a with trimethyl orthoformate in the presence of a catalytic acid such as p-toluenesulfonic acid, gives the dimethyl acetal 3-2. Conversion of 3-2 to 3-3 can be achieved through alkylation or aldol condensation as shown in Scheme 1A. Conversion of esters 3-3 to the carboxylic acids 3-4 can be achieved by a number of conditions depending on the nature of the ester. For example, methyl or ethyl esters can be readily saponified with sodium hydroxide, or lithium hydroxide; benzyl ester can be cleaved through palladium catalyzed hydrogenolysis. These conditions of ester removal are especially advantageous when Intermediates 3-3 were synthesized from Intermediate 3-2 by an alkylation reaction. Coupling of the acid 3-4 with amine 1-5 gives amide 3-5 can be accomplished by the standard amide bond formation conditions, as discussed above. Removal of the dimethyl acetal protecting group from 3-5 can be accomplished by treatment of the acetal 3-5 with an acid such as TFA or hydrogen chloride. Intermediate 1-7a can be then easily converted to the compound of formula Ia in a reductive amination step as described in Scheme 1.

SCHEME 3A

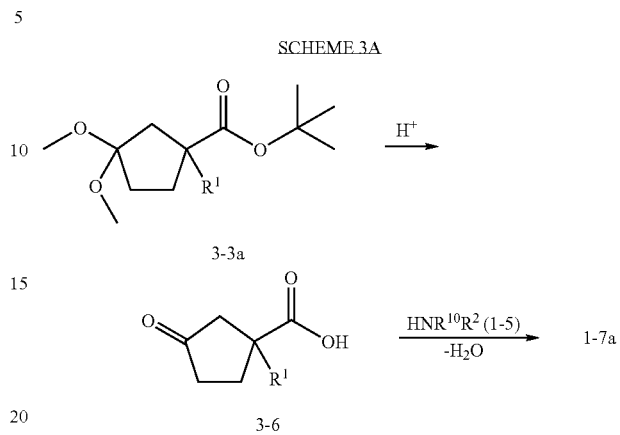

In the case where $R^{13}$ in 3-3 is tert-butyl (3-3a in Scheme 3A), the removal of the ester and the acetal groups can conveniently accomplished in an one-pot operation using acids, such as TFA or hydrogen chloride as reagent, applied neat or in an appropriate solvent, as depicted in Scheme 3A. Conversion of the intermediate keto-acids 3-6 to the respective keto-amids 1-7a could be accomplished under standard amide-bond forming conditions, as described above. The synthesis of the present compounds follows the above described conditions.

SCHEME 4

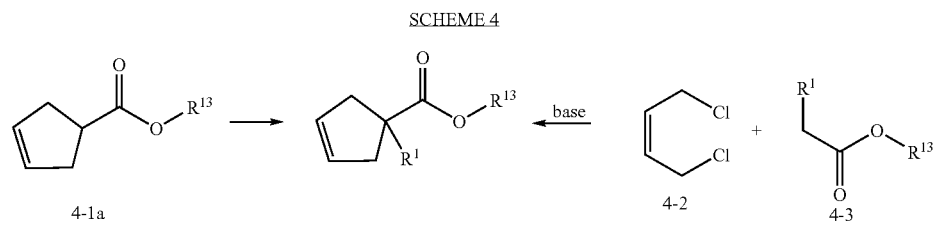

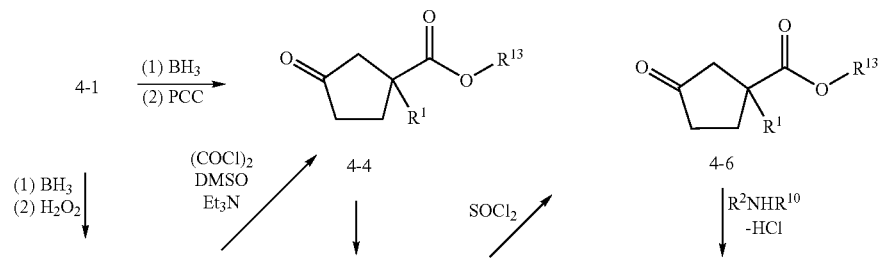

Scheme 4 shows an alternative method in the preparation of the intermediate keto acid 3-6. The readily available 3-cyclopentene-1-carboxylate 4-1a (Depres, J.-P.; Greene, A. E. J. Org. Chem. 1984, 49, 928-931) can be alkylated according to the procedures from Scheme 1A to give compound 4-1. The same intermediate 4-1 can be synthesized by a ring-forming reaction, in which the substituted acetic ester 4-3 is dialkylated with cis-1,4-dichloro-2-butene 4-2 using a strong base such as sodium hydride, sodium, lithium or potassium hexamethyl-disilazide, lithium diisopropylamide, and the like in an appropriate solvent such as DMF, DMPU, DME or a mixture of them (Depres, J.-P.; Greene, A. E. J. Org. Chem. 1984, 49, 928-931).

Hydroboration of olefin 4-1, followed by oxidation with PCC affords the ketone 4-4. Replacing the PCC in the previous sequence by milder hydrogen peroxide, the Intermediate alcohols 4-5 could be obtained. Their oxidation, e.g. by DMSO and oxalyl chloride/triethylamine (Mancuso, A. J., Huang, S-L., Swern, D. *J. Org. Chem.*, 43, 2480 (1978)) afforded the above mentioned keto-esters 4-4 which could be transformed into the carboxylic acids 3-6 by a number of conditions depending on the nature of the ester. For example, methyl or ethyl esters can be readily saponified with sodium hydroxide, or lithium hydroxide; benzyl ester can be cleaved through palladium catalyzed hydrogenolysis; tert-butyl ester can be removed by treatment with TFA. The acids 3-6 were coupled with amines 1-5 as described above to form Intermediates 1-7a.

Alternatively, under standard acid-chloride forming reaction conditions (e.g. thionyl chloride, oxalyl chloride and such), intermediates 3-6 could be converted into the respective acyl chlorides 4-6, and reacted with amines 1-5 to form the keto amides 1-7a. The last reaction required a presence of an appropriate base in order to neutralize the forming hydrogen chloride.

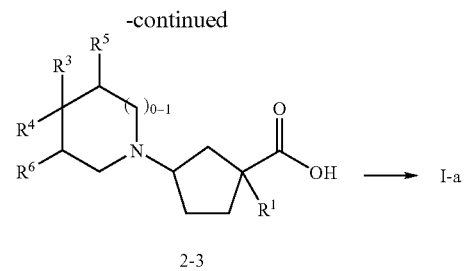

2-3

As depicted in Scheme 5, the intermediate amino acids 2-3 could be prepared starting from nitrites 5-1 (similarly to the synthetic sequence described in Scheme 2). Alkylation of the nitrile 5-1 with cis-1,4-dichloro-2-butene (4-2) as described in Scheme 4, affords the cyclic nitrile 5-3. Hydroboration, followed by oxidation affords the ketone 5-3. Reductive amination with amine 1-8 under the aforementioned conditions yields the amino nitriles 5-4, conversion of which to the corresponding carboxylic acid 2-3 can be achieved by stirring at reflux with a base such as sodium hydroxide in a protic solvent such as ethanol and water. Once again, the respective cis- and trans diastereoisomeric acids formed in the hydrolysis step can be conveniently separated by crystallization (or trituration) of the crude acid mixtures with appropriate protic or aprotic solvents, such as water, alcohols, ketones, various chlorinated solvents, DMF, DMSO or mixtures thereof. Transformation of 2-3 to the compound of formula Ia can then be achieved by amide formation reactions with 1-5 as described in Scheme 1.

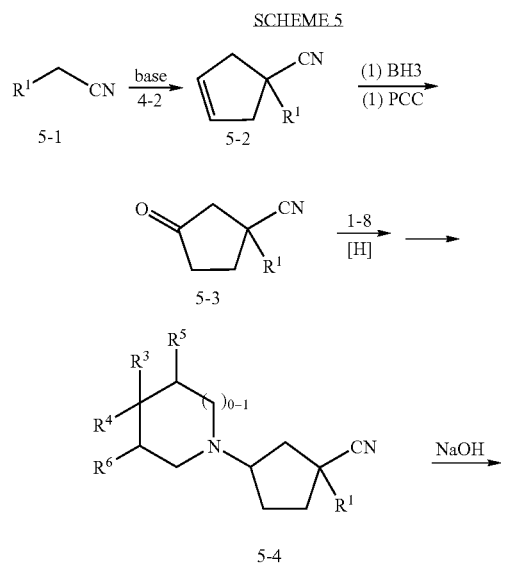

SCHEME 5

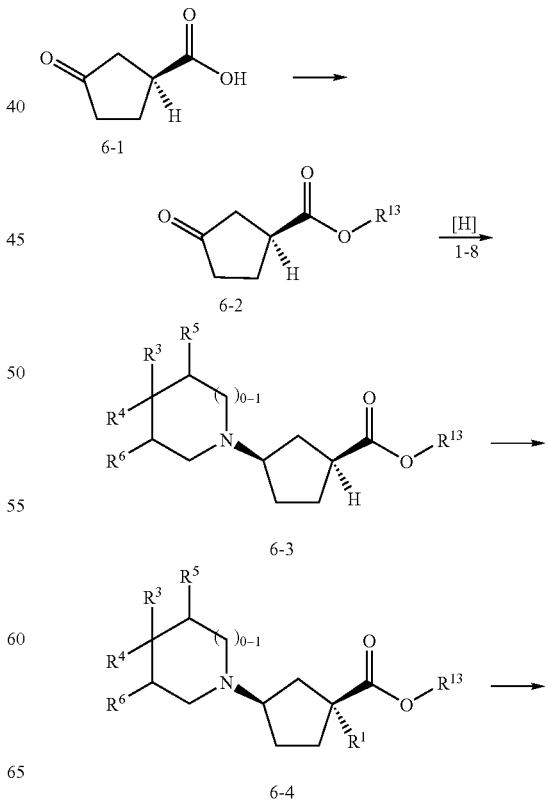

SCHEME 6

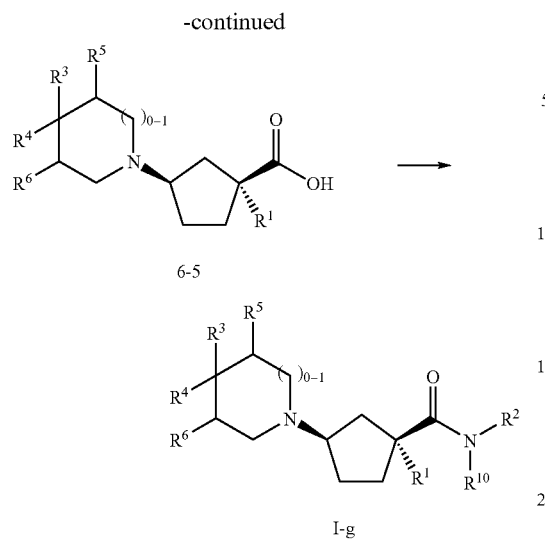

6-5

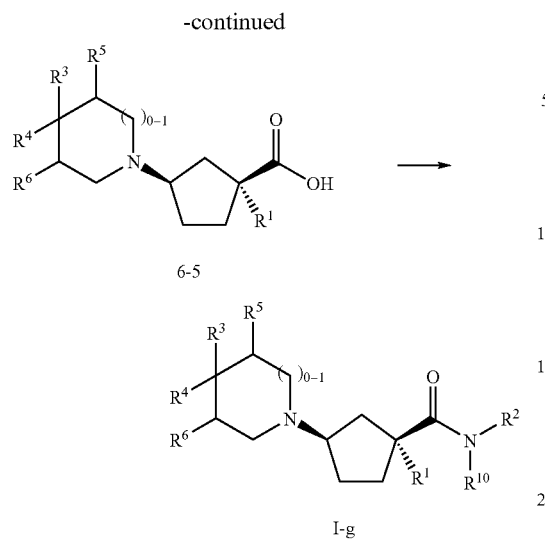

I-g

Scheme 6 shows the preparation of optically pure compounds from optical pure (S)-3-oxocyclopentane carboxylic acid 3-1a (Sung, S-Y., Frahm, A. W., *Arch. Pharm. Med. Chem.*, 1996, 329, 291-300). Acid 6-1 is protected as its ester 6-2 under conditions described in Scheme 3 for the racemic material. Reductive amination with amine 1-8 gives a mixture of cis and trans diastereoisomers, which are homochiral at carbon C1 of the cyclopentane ring. These can be readily separated by column chromatography into the homochiral cis- and homochiral trans-enantiomer. This separation can be performed in the later stage of the synthesis: after the reductive amination step the ester protecting group can be removed and the resulting amino acid can be separated by crystallization, where the desired cis isomer preferably crystallizes over its trans epimer in a variety of solvents. The acid can then be converted back to the ester 6-3 under above mentioned esterification conditions. Alkylation of the ester 6-3 under conditions described in Scheme 1A affords homochiral material 6-4 after chromatographic separation from the trans isomer. Once again, the separation of the cis- and trans isomers could be achieved after the ester protecting group was removed by simple crystallization under conditions similar to those mentioned above.

Converting the ester 6-4 to acid 6-5 is accomplished by appropriate conditions depending on the nature of the ester. Transformation of the chiral acid 6-5 to the compound I-g is accomplished according to the aforementioned conditions.

SCHEME 7

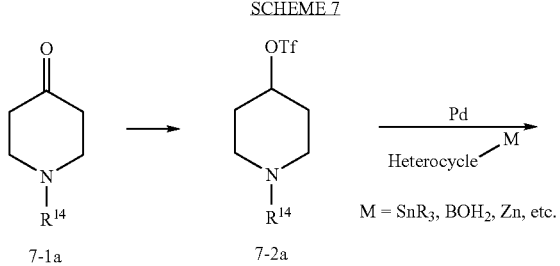

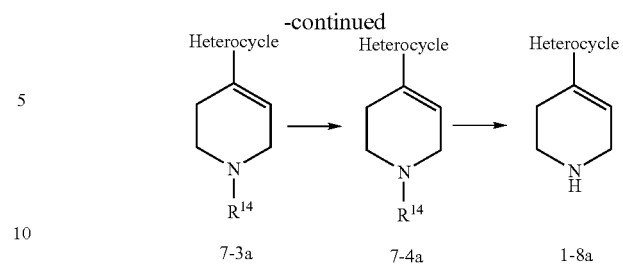

Amines 1-8 may be commercially available or may be prepared according to a variety of known approaches from the literature. One approach we have used is outlined in Scheme 7 and is derived from the literature report of Wustrow and Wise (Wustrow, D. J., Wise, L. D. *Synthesis* 1991, 11, 993.). 4piperidones 7-1a where $R^{14}$ could be one of a variety of protecting groups such as Boc can be converted to their enol-triflate 7-2a using, for example, N-phenyltrifluoromethanesulfonimide. Transition metal mediated coupling (for example with Pd(PPh$_3$)$_4$) of heteroarylboronic acids or stannanes with 7-2a gives compounds 7-3a. Reduction of the olefin can be accomplished by a variety of means, for example with H$_2$ gas in methanol or ethyl acetate and catalytic Pd/C to give 4-heteroarylpiperidines 7-4a. Removal of the protecting group $R^{14}$ depends on the nature of the protecting group; in the case of a t-butoxycarbonyl group treatment with TFA in DCM or HCl in dioxane gives the amines 1-8a. Intermediates 7-3a may also be prepared in two steps by addition of Grignard reagents or heteroaryl lithium reagents to compounds 7-1a (where $R^{14}$ is, for example, benzyl), followed by acid mediated dehydration.

SCHEME 7A

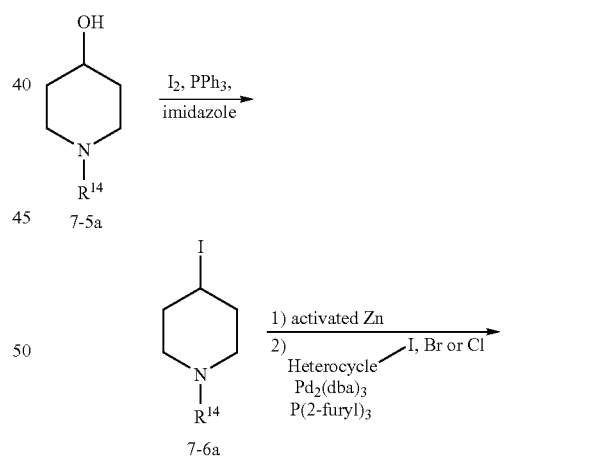

Alternatively intermediates such as 7-4a can be prepared from piperidinols 7-5a Conversion of 7-5a to iodides 7-6a can be accomplished by a number of methods including treatment with I$_2$, PPh$_3$, and imidazole in acetonitrile. Preparation of the organozinc reagent and transition metal mediated coupling to a variety of heteroaryl halides was achieved according to the procedure of Billotte (Billotte, S. *Synlett* 1998, 379.).

SCHEME 8

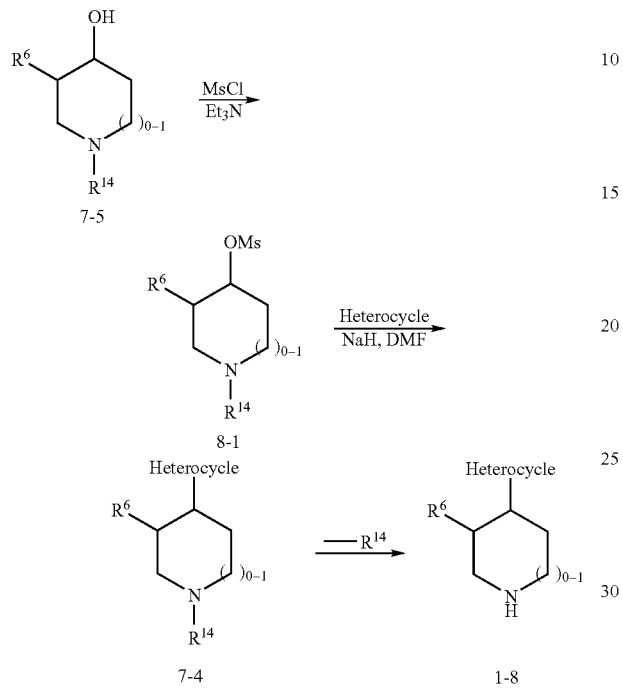

Amines 1-8 may alternatively be prepared according to Scheme 8. Protected hydroxyamines 7-5 are converted into their mesylates using standard conditions. Displacement with heterocycles with active NH groups is accomplished with a base such as sodium hydride in DMF or another appropriate solvent to give 7-4. Removal of the protecting group R$^{14}$ is accomplished using standard conditions depending on the nature of the protecting group; for example t-butoxycarbonyl is removed with TFA/DCM or with HCl in dioxane to give 1-8.

Other amines 1-8 were prepared in a variety of ways, some of which are known from the literature, and some are described in detail in the experimental section of this document.

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230-400 mesh). NMR spectra were obtained in CDCl$_3$ solution unless otherwise noted. Coupling constants (J) are in hertz (Hz). Abbreviations: diethyl ether (ether), triethylamine (TIEA), N,N-diisopropylethylamine (DIEA) saturated aqueous (sat'd), room temperature (rt), hour(s) (h), minute(s) (min).

The following are representative Procedures for the preparation of the compounds used in the following Examples or which can be substituted for the compounds used in the following Examples which may not be commercially available.

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried but on a rotary evaporator under reduced pressure. Flash chromatography was carried out on silica gel (230-400 mesh). NMR spectra were obtained in CDCl$_3$ solution unless otherwise noted. Coupling constants (J) are in hertz (1). Abbreviations: diethyl ether (ether), triethylamine (IEA), N,N-diisopropylethylamine (DIEA) saturated aqueous (sat'd), room temperature (rt), hour(s) (b), minute(s) (min).

The following are representative Procedures for the preparation of the compounds used in the following Examples or which can be substituted for the compounds used in the following Examples which may not be commercially available.

Intermediate 1

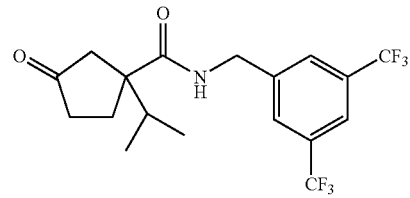

Step A

Methyl 3-Methylene-1-isopropylcyclopentane carboxylate

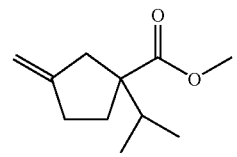

A solution of diisopropylamine (530 µL, 3.76 mmol) in tetrahydrofuran (15 mL) was cooled to −78° C. and nBuLi (1.50 mL, 3.76 mmol, 2.5 M sol. in hexanes) was added via syringe. The neat methyl 3-methylenecyclopentane carboxylate was added via syringe 15 minutes later, and the stirring at −78° C. was continued for another 30 minutes. Isopropyl bromide (921 µL, 9.81 mmol) was injected, and the resulting solution was allowed to warm up to +5° C. overnight and stirred at room temperature for additional 8 hrs. The reaction was quenched with a sat. solution of ammonium chloride (50 mL) and extracted with diethyl ether (2×50 mL).

The combined organic extracts were washed with water (2×40 mL), brine (1×40 mL), dried (anh. magnesium sulfate) and the solvent was evaporated under reduced pressure (80 torr) to yield 340 mg (57%) of product with satisfactory purity. $^1$H NMR (500 MHz, CDCl$_3$) 4.86 (bs, 1H), 4.81 (bs, 1M), 3.67 (s, 3H), 2.87 (bd, 16.7 Hz, 1H), 2.29 (m, 3H), 1.90 (m, 1H), 1.60 (m, 1H), 1.34 (d, 6.2 Hz, 1H), 0.93 (d, 3.7 Hz, 3H), 0.91 (d, 3.7 Hz, 3H).

Step B: 3-Methylene-1-isopropylcyclopentanecarboxylic acid

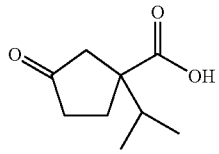

A solution of the methyl 3-methylene-1-isopropylcyclopentanecarboxylate (Step A, 1.21 g, 6.64 mmol) in a mixture of dioxane (4 mL) and water (4 mL) containing 1.114 g (26.56 mmol) of lithium hydroxide monohydrate was homogenized with methanol, and stirred at 80° C. for 48 hrs. The solvent was removed in vacuo, the residue was dissolved in water and the non-acidic components were extracted with diethyl ether (3×30 mL), combined ethers were back-washed with water (1×30 mL). The combined aqueous phases were acidified with 2N HCl and extracted with chloroform (6×30 mL), dried (anhydrous magnesium sulfate) and evaporated to dryness to leave 1.25 g of crude acid. It was used in the next reaction step without any further purification.

Step C: 3,5-Bis(trifluoromethyl)benzyl 3-methylene-1-isopropylcyclopentanecarboxamide

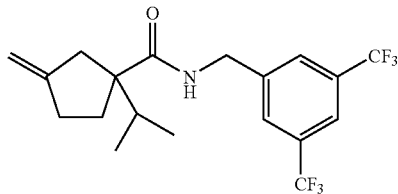

The solution of 3-methylene-1-isopropylcyclopentanecarboxylic acid from the previous step (1.25 g, 7.44 mmol) 3,5-bis(trifluoromethyl)benzylamine hydrochloride (2.08 g, 7.44 mmol), dimethylaminopyridine (111.0 mg, 0.91 mmol) and diisopropylethylamine (1.29 mL, 7.44 mmol) and 1-[3-(dimethylamino)propyl]-3-ethylcarbodiimide hydrochloride (EDC, 2.85 g, 14.9 mmol) in dichloromethane (50 mL) was stirred at room temperature for 24 hrs. The reaction mixture was diluted with dichloromethane (100 mL) and washed with water (3×50 mL), brine (1×50 mL), dried (anhydrous sodium sulfate) and the solvent was evaporated under reduced pressure. The crude product was purified via mplc (Lobar Fertigsaule, LiChroprep, 40-63 μm, ethyl acetate/hexanes (1:4)) yielding 910 mg (31%) of pure product. 1H NMR (500 MHz, CDCl$_3$): 7.76 (s, 1H1), 7.70 (s, 2H), 6.20 (bs, 1H), 4.95 (bs, 1H), 4.88 (bs, 1H), 4.65 (dd, J=15.70, 6.40 Hz, 1H), 4.50 (dd, J=15.50, 5.70 Hz, 1H), 2.68 (bd, J=16.20 Hz, 1H), 2.50 to 2.10 (bm, 4H), 1.96 (h, J=6.9 Hz, 1H), 1.74 (m, 1H), 0.87 (d, J=6.9 Hz, 3H), 0.85 (d, J=7.3 Hz, 3I).

Step D: 3,5-Bis(trifluoromethyl)benzyl 3-oxo-1-isopropyl-cyclopentane-carboxamide

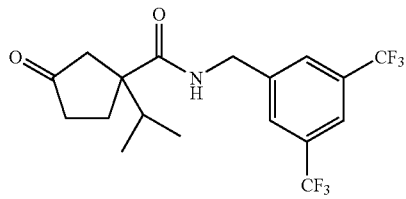

A solution of 3,5-bis(trifluoromethyl)benzyl 3-methylene-1-isopropylcyclopentane-carboxamide (910 mg, 2.31 mmol) in dichloromethane (50 mL) was cooled to −78° C. and a stream of ozone was passed through until the permanent blue color indicated complete consumption of the olefin. The excess ozone was purged with a stream of nitrogen, and triphenylphosphine (729 mg, 2.78 mmol) was added. The cooling bath was removed, and the reaction mixture was allowed to stir at ambient temperature overnight. The solvent was removed in vacuo, the residue was purified by column chromatography (silica gel, ethyl acetate:hexane/1:2) to give 760.7 mg (83%) of the desired product. $^1$H NMR (500 MHz, CDCl$_3$): 7.81 (s, 1H), 7.74 (s, 2H), 6.16 (bs, 1H), 6.61 (m, 2H), 2.78 (bd, J=18.07 Hz, 1H), 2.40 to 2.20 (bm, 4H), 2.08-1.98 (m, 2H), 0.99 (d, J=6.86 Hz, 3H), 0.97 (d, J=6.87 Hz, 3H).

Intermediate 2

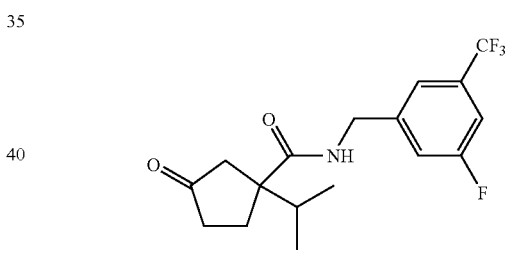

Step A

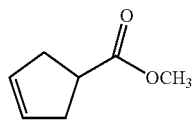

To a solution of 3-cyclopentene-1-carboxylic acid (Org. Synth. 75, p 195-200, 1998) (31.5 g, 281 mmol) in anhydrous N,N-dimethylformamide (300 mL), under an atmosphere of nitrogen, was added potassium carbonate (97 g, 703 mmol), and iodomethane (35 mL, 563 mmol). The resulting mixture was stirred at room temperature for 16 hours, then poured into water (1 litre), and extracted with diethyl ether (3×400 mL). The combined diethyl ether layers were washed with water (3×500 mL), saturated NaCl (200 mL), dried over MgSO$_4$, filtered and concentrated in vacuo, to give 34 g (96%) of crude product. H NMR (CDCl$_3$, 500 MHz): δ 5.64 (s, 2H), 3.68 (s, 3I), 3.11 (quintet, J=8.5 Hz, 1H), 2.63 (d, J=8.3 Hz, 4 H).

Step B

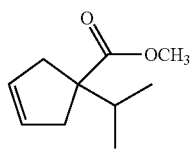

To a cooled (−78° C.) solution of diisopropylamine (34.4 mL, 0.25 Mol) in anhydrous tetrahydrofuran (250 mL) under an atmosphere of nitrogen was slowly added butyl lithium (100 mL of a 2.5M solution in hexanes, 0.25 Mol), and the resulting mixture stirred at −78° C. for 10 min. To this mixture was added methyl-3-cyclopentenecarboxylate (25.75 g, 0.2 Mol), after stirring for a further 15 min 2-iodopropane (41 mL, 0.409 Mol) was added, and the mixture continued stirring at −78° C. for 30 min then allowed to rise to +4° C. and left standing at this temperature for 72 hours. The reaction mixture was poured into 5% citric acid (700 mL) solution and extracted with diethyl ether (3×300 mL). The combined diethyl ether layers were washed with water (2×500 mL), saturated NaCl (1×100 ml), dried over MgSO$_4$, filtered and concentrated in vacuo. The residue was purified by vacuum distillation 50° C. @ 5 mm Hg to provide 28.9 g (86%) of product. H NMR (CDCl$_3$, 500 MHz): δ 5.54 (s, 2H), 3.67 (s, 3H), 2.85 (d, J=15.1 Hz, 2H), 2.30 (dd, J=14.9 Hz 21), 2.07 (quintet, J=6.6 Hz, 1H), 0.82 (d, J=6.6 Hz, 6H).

Step C

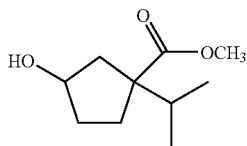

To a cooled (0° C.) solution of borane-methyl sulfide (20 mL, 200 mmol) in anhydrous tetrahydrofuran (100 mL), under an atmosphere of nitrogen, was added using a canula, a solution of cyclopentene ester prepared in step B (28.9 g, 172 mmol). After complete addition the reaction mixture was stirred at room temperature for 20 hours. The mixture was cooled in an ice bath and sodium hydroxide (60 mL of a 3N solution, 181 mmol) added dropwise, followed by 30% hydrogen peroxide (65 mL) and the resulting mixture stirred at 40° C. for 1 hour. The mixture was poured into water (600 ml) and extracted with diethyl ether (3×200 mL), the combined diethyl ether layers were washed with water (3×500 mL), saturated NaCl (100 mL), dried over MgSO$_4$, filtered and concentrated in vacuo. The residue was purified by column chromatography on silica elution with 20% EtOAc/hexanes to give 18.5 g (58%) of product.

Step D

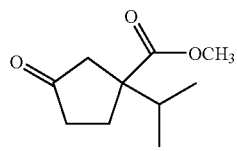

To a (−78° C.) solution of oxalyl chloride (55 mL of a 2M solution in dichloromethane, 109 mmol) in anhydrous dichloromethane (300 mL) under an atmosphere of nitrogen was added in a dropwise manner dimethyl sulfoxide (15.5 mL, 219 mmol), and the resulting mixture stirred at −78° C. for 10 mins. To this mixture was added, using a canula, a solution of the product from step C (18.5 g, 99 mmol) in anhydrous dichloromethane (100 mL). The reaction mixture was stirred at −78° C. for a further 15 mins, then triethylamine (69 mL, 497 mmol) was added and the resulting mixture was allowed to rise to room temperature over 2 hours. The reaction mixture was washed with water (500 mL), saturated NaCl (150 mL), dried over MgSO$_4$, filtered and concentrated in vacuo, to give 18 g, which was used in the next step without further purification.

Step E: 3-Oxo-1-isopropylcyclopentanecarboxylic acid

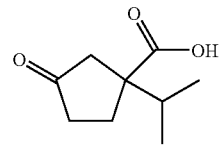

A solution of methyl 3-oxo-1-isopropylcyclopentanecarboxylate (27 g, 146.6 mmol) in dioxane (300 mL) and conc HCl (100 mL) was heated to reflux overnight. The crude product was extracted into diethyl ether (4×200 mL) and the combined organic extracts were washed with an aqueous solution of sodium hydroxide (5N, 2×150 mL). The combined aqueous extracts were cooled to 0° C. and acidified with conc HCl. The product was extracted with ether (3×200 mL), dried with magnesium sulfate and the solvent was evaporated in vacuo. The weight of the product was 20 g (98%). $^1$H NMR (500 MHz, CDCl$_3$): 2.81 (d, J=8.54 Hz, 1H), 2.48 (m, 1H), 2.32 (m, 2H), 2.15 (d, J=18.53 Hz, 1H), 2.08 (m, 1H), 1.95 (m, 1H), 1.03 (d, J=6.86 Hz, 3H), 0.96 (d, J=6.87 Hz, 1H).

Step F: 1-Isopropyl-3-oxocyclopentanoyl chloride

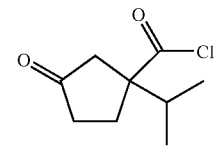

A solution of 1-isopropyl-3-oxocyclopentylcarboxylic acid (20.1 g, 118.9 mmol) in benzene (150 mL) was slowly treated with thionyl chloride (23.5 mL, 322.1 mmol) and the resulting solution was stirred at 45° C. for 3 hours. The solvent and the volatile components were evaporated under reduced pressure (100 torr) and the residue was distilled to obtain 6.727 g (30%) of the desired product, B.P.: 110-114° C. at 5 torr. $^1$H NMR (500 MHz, CDCl$_3$): 2.82 (dd, J=18.36, 1.76 Hz, 1H), 2.50 (m, 1H), 2.35 (m, 2H), 2.20 to 190 (bm, 3H), 1.03 (bd, J=8.2 Hz, 6H).

Step G: 3-Fluoro-5-trifluoromethylbenzyl 3-oxo-1-isopropylpentane-carboxamide

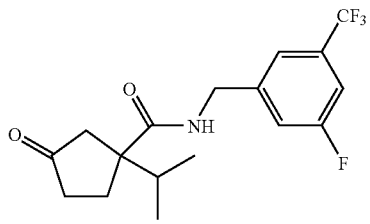

A solution of 3-fluoro-5-trifluoromethylbenzylamine (3.07 g, 15.9 mmol) and diisopropylethylamine (2.77 mL, 15.9 mmol) in dichloromethane (60 mL) was slowly treated with 1-isopropyl-3-oxocyclopentanoyl chloride (3.0 g, 15.9 mmol) and stirred at ambient temperature overnight. The mixture was diluted with dichloromethane washed with a saturated solution of sodium bicarbonate, 2N HCl, water and brine. The organic phase was dried with anhydrous magnesium sulfate and the solvent was evaporated in vacuo to yield 6.0 g of crude product. This was further purified by column chromatography (silica gel, ethyl acetate hexane (40:60%) to yield 4.10 g (85%) of the pure product. $^1$H NMR (500 MHz, CDCl$_3$): 7.32 (s, 1H), 7.23 (d, J=8.23 Hz, 1H), 7.19 (d, J=8.93 Hz, 1H), 4.52 (m, 2H), 2.79 (d, J=18.53 Hz, 1H), 2.40 to 2.18 (bm, 4H), 2.0 (m, 2H), 0.98 (d, J=6.63 Hz, 3H), 0.96 (d, 6.60 Hz, 3H).

Intermediate 3

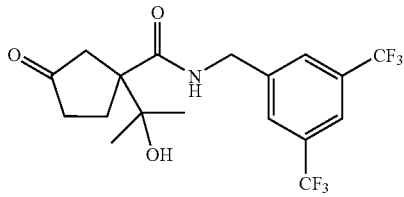

Step A:

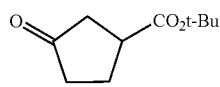

A stirring suspension of MgSO$_4$ (92.1 g, 0.765 mol) in 570 mL of DCM was treated with a mixture of concentrated H$_2$SO$_4$ (10.2 mL, 0.191 mol) in 195 mL of DCM. After five minutes 3-oxo-cyclopentane carboxylate (24.5 g, 0.191 mol) was added. Fifteen minutes later t-butanol (87 g, 1.2 mmol) was added and the resulting mixture was sealed tightly with a stopper and stirred at room temperature over the weekend. The reaction mixture was washed three times with saturated Na$_2$CO$_3$ solution and twice with water. The organic layer was combined with the organic phase of a second identical reaction run simultaneously (starting from 30.1 mmol of carboxylic acid). The combined organic layers were then washed with brine, dried over anhydrous MgSO$_4$, filtered, and concentrated to give 82.8 g of desired t-butyl ester product contaminated with a small amount of t-butanol. $^1$H NMR (500 Mz, CDCl$_3$): 3.02 (m, 1H), 2.47 (dd, J=19, 8 Hz, 1H), 2.38 (m, 3H), 2.26 (m, 1H), 2.20 (m, 1H), 2.09 (m, 1H), 1.46 (s, 9H).

Step B:

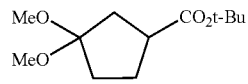

The ketone prepared as described in Step A above (41.0 g, 0.223 mol) was combined with trimethylorthoformate (146 mL, 1.34 mol) and p-TsOH.H$_2$O (2.15 g) in 1:1 DCM/MeOH (200 mL) and stirred at rt overnight. The reaction mixture was washed with 10% Na$_2$CO$_3$ solution twice. The aqueous layer was back-extracted with more DCM. The combined organic layers were washed with water, then brine, dried over anhydrous Na$_2$SO$_4$, filtered, and concentrated to give 61.3 g of crude product. This material was combined with two other batches of crude product prepared in an identical fashion giving 161.7 g total crude product, which was then distilled (107° C. at 5 mm Hg) to give 90.9 g of dimethoxy acetal product. $^1$H NMR (500 Mz, CDCl$_3$): 3.22 (s, 3H), 3.20 (s, 3H), 2.79 (m, 1H), 2.08 (dd, J=13, 9 Hz, 1H), 2.02 (dd, J=13, 9 Hz, 1H), 1.95-1.80 (m, 4H), 1.45 (s, 9H).

Step C:

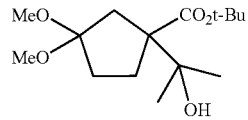

2.5 M n-Butyl lithium in hexanes (28.7 mL, 71.9 mmol) was added dropwise to a cooled (−78° C.) solution of diisopropylamine (10.1 mL, 71.9 mmol) in 10 mL of THF. After stirred the mixture for 30 min, the neat ester prepared as described in Step B above (10 mL, 45 mmol) was added slowly. After stirring at −78° C. for an additional 3 h, 4° A sieves dried acetone (9.9 mL, 135 mmol) was added slowly. After stirring for 1 h, the reaction mixture was quenched with citric acid solution, then extracted with ether. The ethereal layer was washed twice with water and once with brine, dried over anhydrous MgSO$_4$, filtered, and concentrated to give 14.72 g of crude product. Purification by MPLC (silica, 50% ethyl acetate/hexanes) afforded 7.5 g (60%) of hydroxyisopropyl product. $^1$H NMR (400 MHz, CDCl$_3$): 3.49 (s, 3H), 3.43 (s, 3H), 2.39 (m, 2H), 2.25 (m, 2H), 1.83 (m, 3H), 1.48 (s, 3H), 1.46 (s, 9H), 1.41 (s, 3H).

Step D:

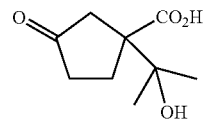

The hydroxyisopropyl ester prepared as described in Step C (1.40 g, 4.85 mmol) was dissolved in 1:1 TFA/DCM (10 mL) and stirred at rt for 2 h. The reaction mixture was concentrated and trace TFA was removed by redissolving in chloroform/hexane and concentrating repeatedly (10 times). The crude product obtained (1.05 g) was used without further purification.

Step E:

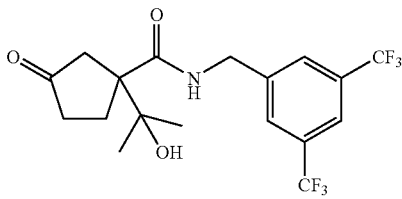

The acid prepared as described in Step D (1.05 g, 5.64 mmol) was combined with 3,5-Bis(trifluoromethyl)benzylamine hydrochloride (1.58 g, 5.64 mmol), EDC (1.62 g, 8.46 mmol), HOAt (768 mg, 5.64 mmol), and DIEA (982 mg, 5.64 mmol) in 60 mL of DCM. The resulting mixture was stirred at rt overnight, then was washed with 1 N HCl, saturated NaHCO$_3$ solution (twice), water (twice), and brine. The organic layer was dried over anhydrous Na$_2$SO$_4$, filtered, and concentrated to give 1.84 g of crude product. Purification by MPLC (silica, 80% ethyl acetate/hexanes) gave 809 mg of ketoamide product. $^1$H NMR (500 MHz, CDCl$_3$): 7.94 (m, 1H), 7.78 (s, 1H), 7.76 (s, 2H), 4.62 (dd, J=15, 6 Hz, 1H), 4.55 (dd, J=16 Hz, 7 Hz, 1H), 2.88 (d, J=18 Hz, 1H), 2.41-2.32 (m, 3H), 2.27-2.19 (m, 2H), 1.34 (s, 3H), 1.28 (s, 3H).

Intermediate 4

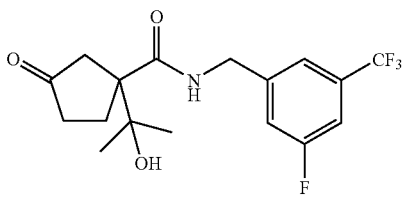

Intermediate 4 was prepared in the same fashion as Intermediate 3, however 3-fluoro-5-trifluoromethylbenzylamine was used in the final amide coupling step instead of Bis(trifluoromethyl)benzylamine hydrochloride.

Intermediate 5

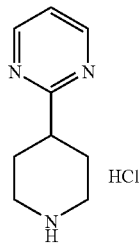

Step A

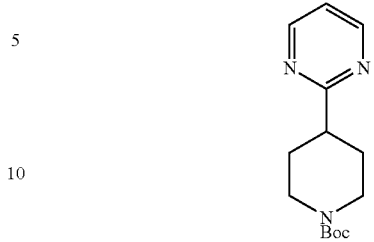

A 3-neck round bottomed flask equipped with an addition funnel and condenser and containing zinc dust (2.45 g, 37.4 mmol) was flame dried. After cooling, and purging the system with nitrogen gas, 6 mL of THF was added, followed by 1,2-dibromoethane (0.298 mL, 3.46 mmol). The mixture was warmed to a vigorous reflux using a heat gun and stirred at reflux for 30 sec (gas evolution was observed), then cooled to rt. The warming and cooling was repeated two more times. Then chlorotrimethylsilane (0.402 mL, 3.17 mmol) was added and the mixture was stirred at rt for 20 min. N-t-butoxycarbonyliodo-piperidine (known: Billotte, S. *Synlett* (1998), 379., 8.97 g, 28.8 mmol) in 15 mL of TBF was added over a period of about 1 min. The reaction mixture was stirred at 50° C. for 1.5 h, then was cooled to rt. Meanwhile, a mixture of tri-2-furylphosphine (267 mg, 1.15 mmol) and Tris(dibenzylideneacetone)-dipalladium(0) chloroform adduct (298 mg, 0.288 mmol) was dissolved in 6 mL of TBF under a nitrogen atmosphere, stirred for 15 min at rt, and added to the organozinc solution. Then a solution of 2-bromopyrimidine (5.50 g, 34.6 mmol) in a mixture of 58 mL of TEF and 20 mL of N,N-dimethylacetamide was added. The reaction mixture was warmed to 80° C. and stirred for 3.5 h, then was cooled to rt and stirred for 36 h. The reaction mixture was filtered through celite and the filter cake was washed with ethyl acetate. The filtrate was diluted further with ethyl acetate, and washed with saturated NaHCO$_3$ solution. The aqueous layer was back extracted with ethyl acetate, the organic layers were combined and washed twice with water and once with brine.

The organic phase was dried over anhydrous MgSO$_4$, filtered, and concentrated. Purification by flash chromatography (silica, stepwise gradient: 25% ethyl acetate/hexane, 40% ethyl acetate/hexane, 60% ethyl acetate/hexane, 80% ethyl acetate/hexane, 100% ethyl acetate) to afford 4.92 g of pure 4-(2-pyrimidyl)-piperidine product (65%). $^1$H NMR (500 MHz, CDCl$_3$): δ 8.70 (d, J=5.0 Hz, 2H), 7.16 (app t, J=4.5 Hz, 1H), 4.24 (brs, 2H), 3.05 (m, 1H), 2.89 (br m, 2H), 2.01 (br d, J=13 Hz, 2H), 1.84 (dq, J=4.5, 12.5 Hz, 2H), 1.49 (s, 9H).

Step B

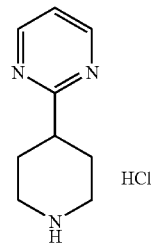

The N-t-butoxycarbonylpiperidine prepared in Step A (4.64 g, 17.6 mmol) was dissolved in 4 N HCl in dioxane (50 mL) and stirred at rt for 2.25 h. The reaction mixture was concentrated to afford 4.16 g of piperidine hydrochloride (100%) which required no further purification. $^1$H NMR (500 Mz, CD$_3$OD): δ 8.95 (d, J=5.5 Hz, 2H), 7.60 (t, J=5.0 Hz, 1H), 3.53 (dt, J=13, 3.5 Hz, 2H), 3.35 (tt, J=4.0, 11.0 Hz, 1H), 3.20 (br t, J=13.8 Hz, 2H), 2.30 (br d, J=14.0 Hz, 2H), 2.11-2.20 (m, 2H); ESI-MS calc. for C9H13N3: 163; Found: 164 (M+H).

A number of heteroaryl piperidines were prepared using the same or a slightly modified procedure as shown for Intermediate 5. Some of these are listed in the Table below.

TABLE

Heteroarylpiperidines prepared analogously to Intermediate 5

| Intermediate | Piperidine | Calc. MW | ESI-MS found (M + H)+ |
|---|---|---|---|
| 6 | 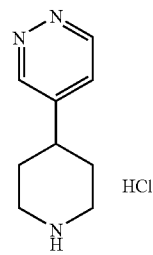 | 163 | 164 |
| 7 | | 163 | 164 |
| 8 | 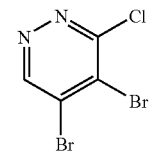 | 197 | 198 |
| 9 | 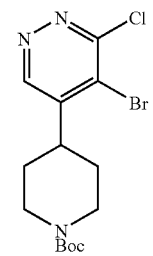 | 197 | 198 |

Intermediate 10

[Structure of pyridazine-piperidine·HCl]

Step A

[Structure of 3-chloro-4,5-dibromopyridazine]

Commercially available 4,5-dibromopyridazine-3-one (5.05 g, 22.3 mmol) was suspended in phosphorus oxychloride (35 mL), warmed to 90° C., and stirred for 3 h. Most of the phosphorus oxychloride was distilled off at 90° C. under reduced pressure. The residue was taken up in DCM and poured into ice. Saturated NaHCO$_3$ solution, followed by 3 N NaOH solution was added until the pH was ~9. The resulting mixture was extracted twice with DCM. The combined organic layers were washed with saturated NaHCO$_3$ solution then brine. The organic layer was then dried over anhydrous MgSO$_4$, filtered, and concentrated to give 5.03 g of product. ESI-MS calc. for C4HBr2ClN2: 270; Found: 271 (M+H).

Step B

[Structure of 3-chloro-4-bromo-5-(N-Boc-piperidinyl)pyridazine]

The 4,5-dibromo-3-chloropyridazine prepared as described in Step A (4.88 g, 17.9 mmol) was coupled to N-t-butoxycarbony-4-iodopiperidine (2.79 g, 8.96 mmol) as described for Intermediate 3 to give 475 mg of desired product contaminated with a small amount of an isomer. $^1$H NMR (500 MHz, CDCl$_3$): δ 8.95 (s, 1H1), 4.34 (br m, 2H), 3.20 (m, 1H), 2.86 (br t, J=12.5 Hz, 2H), 1.90 (m, 2H), 1.69 (m, 2H), 1.51 (s, 9H).

Step C

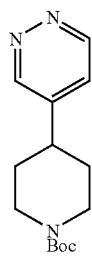

The product from Step B (475 mg, 1.26 mmol) was dissolved in 10 mL of methanol and Pd(OH)$_2$/C (20% Pd, 90 mg) and sodium bicarbonate (212 mg) was added The mixture was stirred under H$_2$ (balloon) for ½ h, filtered and concentrated. The reaction was incomplete so the crude material was resubmitted to the same reaction conditions for an additional 3 h. The reaction mixture was filtered and concentrated. Purification by preparative TLC (silica, 5% methanol/DCM) gave 307 mg of reduced product. $^1$H NMR (500 MHz, CDCl$_3$): δ 9.14 (m, 2H), 7.35 (ap dd, J=3.0, 6.0 Hz, 1H), 4.32 (br m, 2H), 2.85 (br m, 2H), 2.75 (tt, J=4.0, 8.0 Hz, 1H), 1.89 (br d, J=13.5 Hz, 2H), 1.65 (m, 2H), 1.50 (s, 9H).

Step D

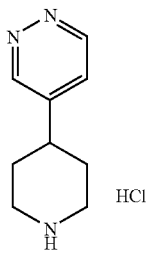

The product from Step C (305 mg, 1.16 mmol) was dissolved in 4 N HCl in dioxane (15 mL) and stirred at rt for 1 h. Then methanol was added (3 mL) and the reaction mixture was stirred for an additional 15 min. The reaction mixture was concentrated to give 244 mg of piperidine hydrochloride (89%). ESI-MS calc. for C9H13N3: 163; Found: 164 (M+H).

Intermediate 11

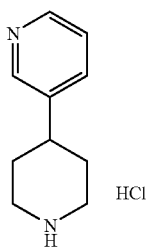

Step A

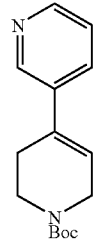

A mixture of 1-t-butoxycarbonyl-4-trifluoromethane-sulfonate-1,2,3,6-tetrahydropyridine (known: Wustrow, D. J., Wise, L. D. *Synthesis* (1991), 993., 2.50 g, 7.53 mmol), triphenylarsine (184 mg, 0.602 mmol), lithium chloride (958 mg, 22.6 mmol) and Tris(dibenzylideneacetone)-dipalladium (0) (138 mg, 0.151 mmol) in anhydrous 1-methylpyrrolidin-2-one (50 mL) was stirred for 5 min, whereupon the reaction color changed from brown/purple to yellow. Then commercially available 3-(tributylstannyl)pyridine (3.27 g, 8.89 mmol) was added in anhydrous 1-methylpyrrolidin-2-one (7 mL). The reaction mixture was purged with argon, stirred at rt for 30 min, at 80° C. for 2.5 h, and at 65° C. for overnight. To the reaction mixture was added 1 M KF solution (15 mL) and the resulting mixture was stirred for 1 h. The reaction mixture was diluted with ethyl acetate and filtered through celite. More 1 M KF solution and ethyl acetate was added to the filtrate. The layers were separated and the aqueous layer was extracted with more ethyl acetate. The combined organic layers were washed six times with water, and once with brine, then were dried over anhydrous MgSO$_4$, filtered, and concentrated. Purification by MPLC (silica, 3% methanol/ethyl acetate) provided 1.09 g (56%) of coupled product. $^1$H NMR (400 MHz, CDCl$_3$): δ 8.63 (d, J=1.6 Hz, 1H), 8.48 (dd, J=4.8, 1.6 Hz, 1H), 7.64 (dt, J=8.0, 2.0 Hz, 1H), 7.25 (obsc m, 1H), 6.08 (br s, 1H), 4.09 (m, 2H), 3.64 (t, J=5.6 Hz, 2H), 2.50 (br s, 2H), 1.47 (s, 9H).

Step B

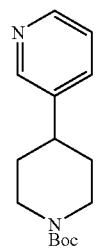

A mixture of 1-t-butoxycarbonyl-4-(3-pyridyl)-1,2,3,6tetrahydropyridine (1.09 g, 4.19 mmol) and Pd(OH)$_2$ (20% Pd on Carbon, 220 mg) in ethanol (20 mL) was stirred under a hydrogen atmosphere (balloon) for 5 h. The reaction mixture was filtered and concentrated, but was found to be incomplete, so was resubmitted to the reaction, this time with 300 mg Pd(OR)$_2$ and under a hydrogen pressure of 50 psi for 7.5 h. The reaction mixture was filtered and concentrated to give 1.12 g of the desired piperidine product. ESI-MS calc. for C15H22N2O2: 262; Found: 263 (M+M).

Step C

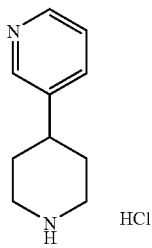

The Boc-piperidine from Step B (1.11 g, 4.23 mmol) was dissolved in 4 N HCl in dioxane (20 mL) and stirred at rt for 1 h. The reaction mixture was concentrated, redissolved in methanol, filtered through a 0.45 µm PTFE filter, and concentrated again to give 950 mg of piperidine hydrochloride. $^1$H NMR (400 MHz, CD$_3$OD): δ 8.90 (d, J=1.6 Hz, 1B), 8.80 (d, J=6.0 Hz, 1H), 8.66 (dt, J=8.4, 2.0 Hz, 1H), 8.11 (dd, J=8.0, 6.0 Hz, 1H), 3.57 (m, 2H), 3.28 (obsc m, 1H), 3.20 (br t, J=13.2 Hz, 2H), 2.21 (m, 2H), 2.05 (m, 2H).

Intermediate 12

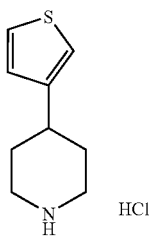

Step A

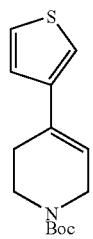

According to literature procedures (Wustrow, D. J., Wise, L. D. *Synthesis* (1991), 9932), N Na$_2$CO$_3$ (7 mL) was combined with 3-thiophene boronic acid (862 mg, 6.73 mmol), lithium chloride (606 mg, 14.4 mmol), 1-t-butoxycarbonyl-4-trifluoromethanesulfonate-1,2,3,6-tetrahydropyridine (1.60 g, 4.81 mmol), and tetrakis(triphenylphosphine)-palladium(0) (555 mg, 0.481 mmol) in DME (17 mL) under a nitrogen atmosphere. The reaction mixture was warmed to reflux and stirred for 2 h. The reaction mixture was concentrated, redissolved in DCM, and washed with 2N Na$_2$CO$_3$ solution, concentrated NH$_4$OH solution, and brine. The organic layer was dried over anhydrous MgSO$_4$, filtered, and concentrated. Purification by flash chromatography (silica, 10% ethyl acetate/hexane) gave 694 mg (55%) of coupled product. $^1$H NMR (500 MHz, CDCl$_3$): δ 7.22 (d, 1H), 7.19 (d, 1H), 7.07 (s, 1H), 6.00 (br s, 1H), 4.03 (br s, 2H), 3.60 (br s, 2H), 2.45 (br s, 2H), 1.47 (s, 9H).

Step B

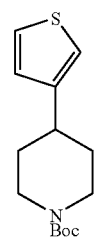

Hydrogenation to the piperidine was accomplished in a similar fashion to that shown in Step B of the synthesis of Intermediate 11 starting from 1-t-butoxycarbonyl-4-(3-thiophene)-1,2,3,6-tetrahydropyridine (694 mg, 2.62 mmol) and providing 540 mg of desired product. ESI-MS calc. for C14H21NO2S: 267; Found. 268 (M+H).

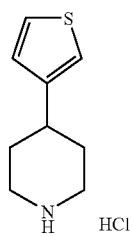

Deprotection was accomplished in a similar fashion to that shown in Step C of the synthesis of Intermediate 11 starting from 1-t-butoxycarbonyl-4-(3-thiophene)-piperidine (540 mg, 2.02 mmol) and providing 408 mg of desired product. ESI-MS calc. for C9H13NS: 167; Found: 168 M+H).

Intermediate 13

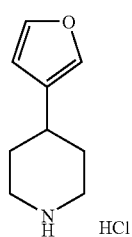

Intermediate 13 was prepared in the same way as described for Intermediate 12. ESI-MS calc. for C9H13NO: 151; Found. 152 (M+H).

Intermediate 14

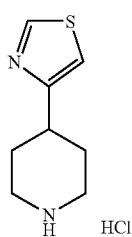

Step A

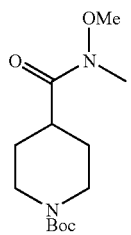

N-Boc-isonipecotic acid (8.04 g, 35.1 mmol) was combined with N,O-dimethylhydroxylamine hydrochloride (5.13 g, 52.6 mmol), EDC (10.1 g, 52.6 mmol) and DIEA (9.2 mL, 53 mmol) in DCM (100 mL). Then N,N-dimethylaminopyridine (~200 mg) was added and the reaction mixture was permitted to stir at rt for 2 h. The reaction mixture was diluted with more DCM and washed with 2 N HCl solution, saturated NaHCO$_3$ solution, and brine. The organic layer was dried over anhydrous MgSO$_4$, filtered, and concentrated to give 8.43 g of crude product which was used without further purification. ESI-MS calc. for C13H24N2O4: 272; Found: 273 (M+H).

Step B

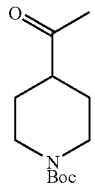

A cooled (−78° C.) solution of the amide prepared as described in Step A (8.35 g, 30.7 mmol) in 100 mL ether was treated dropwise with 3.0 M methylmagnesium chloride in THF (20.4 mL, 61.3 mmol) over a period of five min. The resulting thick slurry was warmed to 0° C. and stirred for 0.5 h. The reaction mixture was poured into 1 N HCl solution and extracted with ether. The ethereal layer was washed with brine, dried over anhydrous MgSO$_4$, filtered, and concentrated to give 5.81 g of crude product which did not require further purification.

Step C

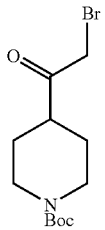

To a cooled (−78° C.) solution of 2.0 M LDA (in heptane/THF/benzene, 13.7 mL, 27.3 mmol) in 100 mL THF was added dropwise over 40 min a solution of the methyl ketone prepared as described in Step B (5.17 g, 22.8 mmol) in 40 mL THF. After an additional 25 min, chlorotrimethylsilane (5.79 mL, 45.6 mmol) was added dropwise over 10 minutes. After stirring the for 1 h, the reaction mixture was poured into 300 mL of saturated NaHCO$_3$ solution and the resulting mixture was extracted twice with 200 mL of ether. The combined ethereal layers were washed with brine, dried over anhydrous MgSO$_4$, filtered, and concentrated to give 7.35 g of TMS-enol ether, which was then redissolved in 120 mL TMF, cooled to 0° C., and treated with sodium bicarbonate (2.87 g, 34.2 mmol), followed by N-bromosuccinimide (4.06 g, 22.8 mmol). The reaction mixture was warmed to rt and stirred for 1 h and 10 min, at which point, it was poured into 200 mL of saturated NaHCO$_3$ solution. The resulting mixture was extracted twice with 200 mL of ether and the combined ethereal layers were washed with saturated NaHCO$_3$ solution and brine, dried over anhydrous MgSO$_4$, filtered, and concentrated to give 7.62 g of crude product which was used without further purification.

Step D

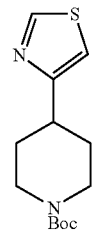

The bromomethylketone prepared as described in Step C (1.48 g, 4.83 mmol) was combined with thioformamide (295 mg, 4.83 mmol) in 10 mL of THF. The reaction mixture was warmed to 60° C. and stirred for 4 days. The reaction mixture was then diluted with ethyl acetate and washed with water, then brine, dried over anhydrous MgSO$_4$, filtered, and concentrated. Purification by MPLC (silica, 60% ethyl acetate/hexane) afforded 627 mg of thiazole product $^1$H NMR (400 MHz, CDCl$_3$): δ 8.75 (d, J=2.0 Hz, 1H), 6.93 (d, J=2.4 Hz, 1H), 4.19 (br s, 2H), 2.96 (m, 1H), 2.84 (br m, 2H), 2.03 (m, 2H), 1.62 (m, 2H), 1.44 (s, 9H).

Step E

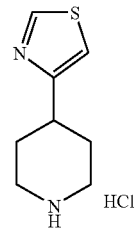

The thiazole prepared as described in Step D (588 mg, 2.19 mmol) was treated with 4 N HCl in dioxane (15 mL). Since the mixture was heterogeneous, 1 mL of water was added to solubilize the starting material and the mixture was stirred for 1.5 h. The reaction mixture was then concentrated to give 526 mg of piperidine hydrochloride. $^1$H NMR (400 MHz, CD$_3$OD): δ 9.60 (d, J=2.4 Hz, 1H), 7.72 (d, J=2.80 Hz, 1H), 3.52 (m, 2H), 3.31 (m, 1H), 3.19 (m, 2H), 2.29 (m, 2H), 1.99 (m, 2H). ESI-MS calc. for C8H12N2S: 168; Found: 169 (M+H).

Intermediate 15

Step A

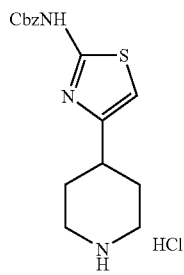

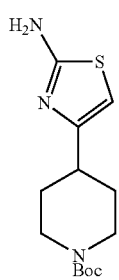

The bromomethylketone prepared as described in Steps A through C of the synthesis of Intermediate 14 (1.68 g, 5.47 mmol) was combined with thiourea (625 mg, 8.21 mmol) and potassium carbonate (1.51 g, 10.9 mmol) in ethanol and the resulting mixture was stirred at 60° C. for 8 h. The reaction mixture was then concentrated and the residue was partitioned between ethyl acetate and water. The aqueous layer was extracted again with ethyl acetate and the combined organic layers were washed with brine, dried over anhydrous MgSO$_4$, filtered, and concentrated to give 1.42 g of crude aminothiazole product.

Step B

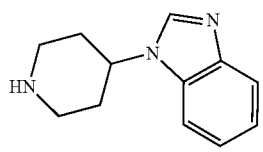

To a cooled (0° C.) solution of the aminothiazole prepared as described in Step A (142 g, 5.01 mmol) and triethylamine (1.19 mL, 8.52 mmol) in 25 mL of DCM was added dropwise benzyl chloroformate (0.858 mL, 6.01 mmol). The reaction mixture was warmed to rt and stirred for 1 h. TLC indicated that the reaction was incomplete so additional portions (as above) of triethylamine and benzyl chloroformate were added and the resulting mixture was stirred for 3 h. The reaction mixture was diluted with DCM and washed twice with water and once with brine. The organic layer was dried over anhydrous MgSO$_4$, filtered, and concentrated. Purification by MPLC (silica, 55% ethyl acetate/hexane) afforded 930 mg of product.

Step C

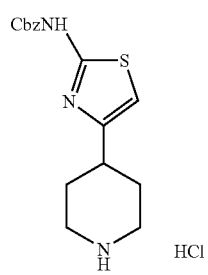

The product from Step B (925 mg, 2.22 mmol) was dissolved in 4 N HCl in dioxane (15 mL) and stirred at rt for 1 h. The reaction mixture was concentrated to give 749 mg of title compound.

ESI-MS calc. for C16H19N3O2S: 317; Found: 318 (M+H).

Intermediate 16

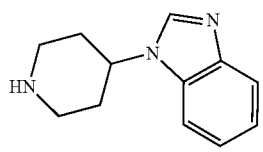

Formic acid (568 mg, 12.3 mmol) was added to Ac$_2$O (1.05 g, 10.3 mmol) at 0° C. and the resulting mixture was warmed to 60° C., stirred for 2.75 h and cooled to room temperature. ThF (5 mL) was then added, the solution was cooled to −15° C., and the 2-(1-t-butoxycarbonylpiperidinylamino)aniline (2.00 g, 6.86 mmol) was added in THF (5 mL). After 0.5 h the reaction mixture was concentrated (with warming at 40° C.) and the resulting crude product was purified by MPLC (silica, 90% ethyl acetate/hexane, then 100% ethyl acetate, then 4% methanol/ethyl acetate) to give 1.25 g of the benzimidazole. The BOC group was removed by dissolving the intermediate (1.21 g, 4.00 mmol) in ethyl acetate and bubbling HCl (g) through this solution for 10 min. The solvent was removed to afford 962 mg of crude Intermediate 10 as its hydrochloride salt.

BOC intermediate: ESI-MS calculated for C17H23N3O2: 301; Found: 302 (M+H).

Intermediate 17

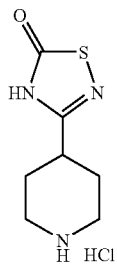

Step A

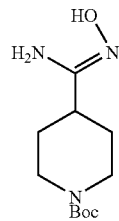

Hydroxylamine hydrochloride (8.26 g, 119 mmol) and triethylamine (16.6 mL, 119 mmol) were combined in 50 Ml of DMSO. The suspension was filtered to remove triethylamine hydrochloride and the filter cake was washed with TBF. The filtrate was partially concentrated to remove the THF. Then commercially available 1-t-butoxycarbonyl-4-cyanopiperidine (5.0 g, 24 mmol) was added to the DMSO solution and the resulting reaction mixture was stirred at 75° C. for 3 h, and at rt for overnight. The reaction mixture was diluted with ethyl acetate and washed with water. The aqueous layer was back-extracted with more ethyl acetate and the combined organic layers were washed four times with water and once with brine. The organic layer was dried over anhydrous $MgSO_4$, filtered, and concentrated to give 3.51 g of product.

Step B

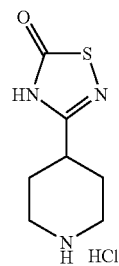

A solution of the intermediate from Step A (1.02 g, 4.19 mmol) in 20 mL THF was treated with thiocarbonyldiimidazole (897 mg, 5.03 mmol), whereupon gas evolution and an exotherm were noted. The reaction mixture was stirred at rt for 1 h, then was transferred to a suspension of silica gel #60 (20 g) in 180 mL of 5:1 $CHCl_3$/methanol. The reaction mixture was stirred at rt for 5 days, then filtered and concentrated. Purification by MPLC (silica, 50% ethyl acetate/hexane) afforded 143 mg of thiodiazolone.

Boc intermediate $^{H\ NMR}$ (500 MHz, $CD_3OD$): δ 4.16 (m, 2H), 2.86 (t, J=11.5 Hz, 2H), 2.77 (tt, J=4.0, 11.0 Hz, 1H), 1.98 (dd, J=2.0, 13.0 Hz, 2H), 1.73 (dq, J=4.5, 12.0 Hz, 21), 1.47 (s, 9H).

The Boc intermediate (139 mg, 0.487 mmol) was dissolved in 4N HCl in dioxane (5 mL) and stirred at rt for 1.5 h. The reaction mixture was concentrated to give 94.3 mg of piperidine hydrochloride product.

Intermediate 18

4-(1H-1,2,4-triazol-1-yl)piperidine hydrochloride

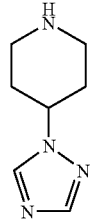

Step A tert-butyl 4-hydroxypiperidine-1-carboxylate

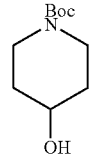

To a stirred solution of 4-hydroxypiperidine (60.8 g) in dichloromethane (500 mL) was added a solution of di-ter-butyl dicarbonate (19.44 g, 0.547 mol) in dichloromethane (500 mL) very slowly. After the addition, which took 1 hour, the resulted mixture was stirred at ambient temperature for 5 hours. The mixture was then washed with saturated $NaHCO_3$, 3 N HCl, brine, dried and evaporated to give tert-butyl 4-hydroxypiperidine-1-carboxylate as a thick oil (90 g).

Step B: tert-butyl 4-[(methylsulfonyl)oxy]piperidine-1-carboxylate

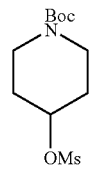

To a stirred solution of: give tert-butyl 4-hydroxypiperidine-1-carboxylate (21.1 g, 0.105 mol) and triethyl amine (22 mL) in dichloromethane (250 mL) at 0° C. was slowly added methanesulfonyl chloride (9 mL, 1.1 equiv.). The resulting mixture was stirred for 1 additional hour and during which time white solid was formed. The mixture was then washed with 3 N HCl, dried over $Na_2SO_4$ and evaporated to give: tert-butyl 4-[(methylsulfonyl)oxy]piperidine-1-carboxylate as a white solid (29.2 g). $^1H$ NMR (400 MHz, $CDCl_3$): 4.92-4.87 (m, 1H), 3.75-3.69 (m, 2H), 3.34-3.28 (m, 2H), 3.05 (s, 3H), 2.01-1.94 (m, 2H), 1.87-1.78 (m, 2H).

Step C: 4-(1H-1,2,4-triazol-1-yl)piperidine hydrochloride

To a stirred solution of: tert-butyl 4-[(methylsulfonyl)oxy] piperidine-1-carboxylate (5.9 g, 21.1 mmol) and 1,2,4-triazole (1.75 g, 1.2 equiv.) in DMF at ambient temperature was added sodium hydride (60% in mineral oil, 1.0 g, 1.2 equiv.). The mixture was stirred at 60° C. for 5 days, and the TLC showed no starting mesylate left. The mixture was poured into ice water and extracted with ethyl acetate (3×). The organic layer was dried, evaporated and purified by silica flash column eluting with 0-10% methanol in ethyl acetate to give tert-butyl 4-(1H-1,2,4-triazol-1-yl)piperidine-1-carboxylate as a white solid. The solid was then treated with hydrogen chloride in dioxane (4 N, 10 mL) for 2 hours. The mixture was then evaporated to remove most of the dioxane to give a white solid, which was washed with ethyl acetate to give the desired 4-(1H-1,2,4-triazol-1-yl)piperidine hydrochloride salt (5.55 g). $^1$H NMR (300 Mz, CD$_3$OD): 10.00 (s, 1H), 8.97 (s, 1H), 5.10-5.00 (m, 1H), 3.63-3.58 (br. d, 2H), 3.33-3.26 (br. d, 2H), 2.50-2.30 (m, 4H).

The following intermediates are prepared in a similar fashion to Intermediate 18 using: tert-butyl 4-[(methylsulfonyl)oxy]piperidine-1-carboxylate and the appropriate heterocycles.

Intermediate 19

4-(1H-pyrazol-1-yl)piperidine hydrochloride

Prepared using pyrazole

Intermediate 20

4-(1H-imidazol-1-yl)piperidine hydrochloride

Prepared from imidazole: $^1$H NMR (400 MHz, CD$_3$OD): 9.18 (s, 1H), 7.86 (s, 1H), 7.65 (s, 1H), 4.9-4.8 (hidden under CD3OD peak, 1H), 3.61-3.61 (br. d., 2H), 3.33-3.26 (m, 2H), 2.49-2.45 (br. d, 2H), 2.39-2.28 (m, 2H).

Intermediate 21 and 22

4-(1H-1,2,3-triazol-1-yl)piperidine hydrochloride and 4-(2H-1,2,3-triazol-2-yl)piperidine hydrochloride Prepared from 1,2,3-triazole.
4-(1H-1,2,3-triazol-1-yl)piperidine hydrochloride: $^1$H NMR (400 MHz, CD$_3$OD):8.77 (s, 1H), 8.54 (s, 1H), 5.26-5.19 (m, 1H), 3.65-3.59 (m, 2H), 3.37-3.29 (m, 2H), 2.60-2.54 (m, 2H), 2.50-2.39 (m, 2H).
4-(2H-1,2,3-triazol-2-yl)piperidine hydrochloride: $^1$H NMR (400 MHz, CD$_3$OD): 7.72 (s, 2H), 4.94-4.87 (m, 1H), 3.54-3.48 (m, 2H), 3.28-3.22 (m, 2H), 2.46-2.32 (m, 4H).

Intermediate 23 and 24

4-(1H-tetraazol-1-yl)piperidine hydrochloride: $^1$H NMR (400 MHz, CD$_3$OD): 8.77 (s, 1H), 5.30-5.23 (m, 1H), 3.58-3.53 (m, 2H), 3.35-3.29 (m, 2H), 2.58-2.2.52 (m, 2H), 2.48-2.38 (m, 2H), 4-(2H-tetraazol-2-yl)piperidine hydrochloride: $^1$H NMR (400 MHz, CD$_3$OD): 9.32 (s, 1H), 5.08-5.00 (m, 1H), 3.61-3.57 (m, 2H), 3.33-3.28 (m, 2H), 2.52-2.47 (m, 2H), 2.42-2.32 (m, 2M)

Intermediate 25

4-(1H-pyrrol-1-yl)piperidine

Prepared similarly with pyrrole.

Intermediate 26

4-(4H-1,2,4-triazol-4-yl)piperidine

Step A: ethyl 4-(4H-1,2,4-triazolyl)piperidine-1-carboxylate
To a stirred solution of ethyl-4-amino-piperidine carboxylate (5 g, 29 mmol) in toluene (100 mL) was added N,N-dimethylformamide azine (8.2 g) and catalytic amount of p-tolunesulfonic acid (0.3 g) and the resulting mixture was refluxed overnight. The mixture was cooled and washed with water, and the aqueous layer was evaporated and the residue was treated with dichloromethane (100 mL). The organic layer was dried over MgSO4, filtered and evaporated. The residue was purified on silica flash column eluting with 4% MeOH, 0.5% NH4OH in dichloromethane to give the desired ethyl 4-(4H-1,2,4-triazol-4-yl)piperidine-1-carboxylate (4.9 g).

Step B: 4-(4H-1,2,4-triazolfyl)piperidine
To a solution of ethyl 4-(4H-1,2,4-triazolyl)piperidine-1-carboxylate (4.9 g) in ethanol (100 mL) was added a solution of potassium hydroxide (10 g in 10 mL of water) and the resulting mixture was refluxed overnight. The mixture was evaporated off and the residue was treated with dichloromethane (100 mL). The solution was filtered and dried over MgSO4, filtered and evaporated to give 4(4H-1,2,4-triazol-4-yl)piperidine (2 g). $^1$H NMR (400 Mz, CDCl$_3$): 8.23 (s, 2 H), 4.17-4.10 (m, 1H), 3.26 (br. d, J=12.5 Hz, 2H), 2.76 (dt, J=2, 12.5 Hz, 2H), 2.13 (br. d, J=12 Hz, 2H), 1.85 (ddd, J=4, 12, 15 Hz, 2H).

Intermediate 27

4-(1H-pyrazol-4-yl)piperidine

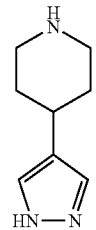

Step A: 4-(1H-pyrazol-4-yl)pyridine
To a suspension of 2-pyridin-4-ylmalonaldehyde (5 g, 33.6 mmol) in ethanol (75 mL) was added hydrazine (1.26 mL, 1.2 equiv.) and the resulting mixture was stirred at room temperature for 4 hours. The mixture was evaporated and the residue tritriated with ether/hexane to give 4-(1H-pyrazolyl)pyridine as a solid (4.8 g).

Step B: 1-benzyl-4-(1H-pyrazol-4-yl)-1,2,3,6-tetrahydropyridine
To a hot (80° C.) solution of 4-(1H-pyrazol-4-yl)pyridine (4.8 g) in 2-propanol was added benzyl bromide (10 mL, 2.5 equiv.) and the resulting mixture heated at reflux for 10 minutes. After cooling in an ice bath, the precipitate was filtered and washed with more 2-propanol and air dried. The solid was suspended in ethanol at 0° C. and sodium borohydride (6.5 g) was added in several portions over 30 minutes, and the mixture was stirred for an additional 30 minutes. The reaction was quenched by carefully addition of water, and the ethanol was removed by evaporation, and the residue was partitioned between dichloromethane and water. The organic layer was dried over MgSO4, and filtrated and evaporation gives 1-benzyl-4-(1H-pyrazol-4-yl)-1,2,3,6-tetrahydropyridine (7.5 g)

Step C: 4-(1H-pyrazol-4-yl)piperidine
A solution of 1-benzyl-4-(1H-pyrazol-4-yl)-1,2,3,6-tetrahydropyridine (7.5 g) was hydrogenated over palladium on carbon (10%, 1 g) at 40 psi overnight. The catalyst was removed by filtration through celite and the filtrate was evaporated. NMR shows the product is mainly 1-benzyl-4-(1H-pyrazol-4-yl)-piperidine.

To a solution of 1-benzyl-4-(1H-pyrazol-4-yl)-piperidine (2 g) and formic acid (10 mL) in ethanol (150 mL) was added palladium on carbon (10%, 0.5 g) and the resulting mixture was stirred at room temperature overnight. The catalyst was removed by filtration and filtrate evaporated. The product was purified by adding di-ter-butyl dicarbonate (2 equiv.) and triethyl amine (1.5 equiv.) in dichloromethane to give a di-Boc protected intermediate. Evaporated and purification by column chromatography on silica eluting with 20% ethyl acetate in hexane give pure tert-butyl 4-[1-(tert-butoxycarbonyl)-1H-pyrazol-4-yl]piperidine-1-carboxylate. The di-Boc intermediate was then treated with methanolic HCl to give 4-(1H-pyrazol-4-yl)piperidine hydrochloride salt (1.3 g). ). $^1$H NMR (400 MHz, CDCl$_3$): 8.00 (s, 2 H), 3.42 (br. d, J=13 Hz, 2H), 3.10 (t, J=13 Hz, 2H), 3.05-2.96 (m, 1H), 2.19 (br. d, J=13 Hz, 2H), 1.80 (m, 2H).

Intermediate 28

4-(1H-pyrazol-3-yl)piperidine

Step A: 4-(1H-pyrazol-3-yl)pyridine

To a mixture of 4-acetylpyridine (75 mL, 0.68 mol) and ethyl formate (109 mL) in anhydrous benzene (1 L) was added sodium methoxide (73 g) and the resulting mixture was refluxed for 18 hours. The mixture was cooled and benzene decanted from a sticky solid, which had formed during the reaction. The crude product was dissolved in water (700 mL) and hydrazine dihydrochloride was added and the resulting mixture was stirred at room temperature for 2 hours. The mixture was redissolved by addition of 5N NaOH. Precipitate formed which was removed by filtration and dried to give 4-(1H-pyrazol-3-yl)pyridine (35 g).

Step B: 1-benzyl-4-(1H-pyrazol-3-yl)-1,2,3,6-tetrahydropyridine

To a hot (80° C.) solution of 4-(1H-pyrazol-3-yl)pyridine (9.6 g) in 2-propanol (60 mL) was added benzyl bromide (20 mL, 2.5 equiv.) and the resulting mixture heated at reflux for 10 minutes. After cooling in an ice bath, the precipitate was filtered and washed with more 2-propanol and air dried. The solid was suspended in ethanol at 0° C. and sodium borohydride (13 g) was added in several portions over 30 minutes, and the mixture was stirred for an additional 30 minutes. The reaction was quenched by carefully addition of water, and the ethanol was removed by evaporation, and the residue was partitioned between dichloromethane and water. The organic layer was dried over MgSO4, and filtrated and evaporation gives 1-benzyl-4-(1H-pyrazol-3-yl)-1,2,3,6-tetrahydropyridine (16 g)

Step C: 4-(1H-pyrazol-3-yl)piperidine

A solution of 1-benzyl-4-(1H-pyrazol-3-yl)-1,2,3,6-tetrahydropyridine (16 g) was hydrogenated over palladium on carbon (10%, 1 g) at 40 psi overnight. The catalyst was removed by filtration through celite and the filtrate was evaporated. NMR shows the product is 1-benzyl-4-(1H-pyrazol-3-yl)-piperidine (16 g).

To a solution of 1-benzyl-4-(1H-pyrazol-3-yl)-piperidine (16 g) and formic acid (30 mL) in ethanol (400 mL) was added palladium on carbon (10%, 2 g) and the resulting mixture was stirred at room temperature overnight The catalyst was removed by filtration and filtrate evaporated. The product was purified by adding di-ter-butyl dicarbonate (2 equiv.) and triethyl amine (1.5 equiv.) in dichloromethane to give a Boc protected intermediate. Evaporated and purification by column chromatography on silica eluting with 20-40% ethyl acetate in hexane give pure tert-butyl 4-(1H-pyrazol-3-yl) piperidine-1-carboxylate. The Boc intermediate was then treated with methanolic HCl to give 4-(1H-pyrazol-3-yl)piperidine hydrochloride salt (3.5 g). Loss of material was due to the formation of di-Boc product, which was not collected. $^1$H NMR (400 MHz, CDCl$_3$): 8.00 (s, 2 H), 3.48 (br. d, J=13 Hz, 2H), 3.28-3.20 (m, 1 H), 3.13 (br. t, J=13 Hz, 21), 2.23 (br. d, J=14 Hz, 2H), 1.97-1.85 (m, 2H).

Intermediate 29

4(1H-imidazol-2-yl)piperidine dihydrochloride

Step A: tert-butyl 4-hydroxy-4-(1H-imidazol-2-yl)piperidine-1-carboxylate

A mixture of imidazole (25.6 g, 0.4 mol), triethyl orthoformate (236.8 g, 1.6 mol) and p-toluenesulfonic acid (2 g) was heated at 130° C. overnight with no condenser so ethanol can boil off. The excess orthoformate was removed by rotary evaporation and the residue was purified by vacuum distillation to give 1-(diethoxymethyl)-1H-imidazole (46.7 g). To a solution of the resulting protected imidazole (46.7 g) in anhydrous THF (350 mL) under N2 cooled at –40° C., was added n-butyllithium (2.5 M in hexane, 110 mL) at such a rate that the temperature did not rise above –35° C. After complete addition, a solution of tert-butyl 4-oxopiperidine-1-carboxylate (18.25 g, 91.5 mmol) in anhydrous THF (70 mL) under N2 was added dropwise over 10 minutes keeping the temperature below –40° C. The reaction was stirred at 40° C. for 2 hours then 350 mL of 0.1 N HCl added and stirred for 15 minutes, ethyl acetate (350 mL) added and stirred for 5 minutes. The organic layer was separated and aqueous extracted with ethyl acetate (350 mL). The combined organic layers were washed with saturated NaHCO3, brine, dried over MgSO4, filtered and evaporated. The residue was purified by column chromatography on silica eluting with 10% methanol in ethyl acetate with 0.5% ammonia hydroxide to give tert-butyl 4-hydroxy-4-(1H-imidazol-2-yl)piperidine-1-carboxylate (10.5 g).

Step B: tert-butyl 4-(1H-imidazol-2-yl)-3,6-dihydropyridine-1(2H)-carboxylate

To a solution of tert-butyl 4-hydroxy-4-(1H-imidazol-2-yl) piperidine-1-carboxylate (10.5 g) and diisopropylamine (13.8 mL, 2.5 equiv.) in anhydrous DMF under N2 at 0° C. was added in one portion of methanesulfonyl chloride (6.19 mL, 2 equiv.). The reaction was stirred at 0° C. for 2 hours when a further 2 equivalents of methanesulfonyl chloride and 2.5 equivalents of diisopropylamine was added and the resulting mixture stirred at room temperature overnight. The mixture was diluted with water (200 mL) and adjusted pH 9 with 1 N NaOH and then extracted with ethyl acetate (3×). The combined ethyl acetate layers was dried over MgSO4, filtered and evaporated. The residue was purified by column chromatography on silica eluting with 5% methanol in dichloromethane with 0.5% ammonium hydroxide to give tert-butyl 4-(1H-imidazol-2-yl)-3,6-dihydropyridine-1(2H)-carboxylate (7.5 g).

Step C: tert-butyl 4-(1H-imidazol-2-yl)piperidine-1-carboxylate

A mixture of tert-butyl 4-(1H-imidazol-2-yl)-3,6-dihydropyridine-1(2H)-carboxylate (7.5 g) and palladium on carbon (10%, 1 g) in ethanol (150 mL) was hydrogenated at 30 psi overnight. The catalyst was removed by filtration through celite and the filtrate was evaporated to give tert-butyl 4-(1H-imidazol-2-yl)piperidine-1-carboxylate (7.5 g).

Step D: 4-(1H-imidazol-2-yl)piperidine dihydrochloride

A solution of tert-butyl 4-(1H-imidazol-2-yl)piperidine-1-carboxylate (5.5 g) in methanol was saturated with HCl and the mixture was left standing overnight. Evaporation give the product in quantitative yield. $^1$H NMR (400 MHz, $D_2O$): 7.29 (s, 2H), 3.51 (br. d, J=13 Hz, 2H), 3.47-3.40 (m, 1H), 3.12 (br. t, J=13 Hz, 2H), 2.29 (br. d, J=14 Hz, 2H), 2.04-1.92 (m, 21).

Intermediate 30

4-(1,3-thiazol-2-yl)piperidine hydrochloride

Prepared similarly as in the case of 4-(1H-imidazol-2-yl)piperidine dihydrochloride using 1,3-thiazole instead of 1-(diethoxymethyl)-1H-imidazole in Step A. $^1$H NMR (400 MHz, $D_2O$): 8.24 (m, 1 H), 7.90(m, 1H), 3.77-3.68 (m, 1H), 3.57 (br. d, J=13 Hz, 2H), 3.19 (br. t, J=13 Hz, 2H), 2.42 (br. d, J=13 Hz, 21), 2.11-2.01 (m, 2H).

EXAMPLE 1

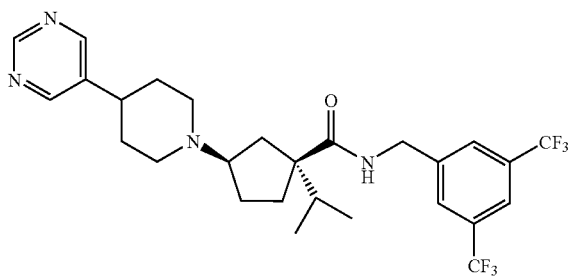

Ketone Intermediate 1 (100 mg, 0.253 mmol) was combined with 4-(5-pyrimidyl)-piperidine hydrochloride (prepared as described for Intermediate 5, 90 mg, 0.38 mmol), triethylamine (105 µL, 0.759 mmol), sodium triacetoxyborohydride (212 mg, 1.00 mmol) and 4° A molecular sieves (powder, 100 mg) in DCM (10 mL). The reaction mixture was stirred at rt for 2 days, then was filtered through a celite plug. The filtrate was concentrated and purified by preparative TLC (silica, 5% of 1:9 NH$_4$OH/methanol in DCM, then a second plate with 10% methanol/DCM) to afford two bands corresponding to the cis (top spot) and trans isomers (bottom spot). Both the cis and trans isomers were converted to HCl salts by dissolving the free bases in ~1 mL of DCM, adding excess 1 N HCl in ether, and concentrating. Top spot-ESI-MS calculated for C27H32F6N4O: 542; Found: 543 (M+H). Bottom spot-ESI-MS calculated for C27H32F6N4O: 542; Found: 543 (M+H). Single cis-enantiomers were obtained via chiral HPLC, using Diacel's Chiralcel AD semipreparative column, eluting with 10% ethanol/hexane (using the free base). The observed retention times of the respective diastereoisomers were 25 and 38 minutes, respectively.

EXAMPLE 2

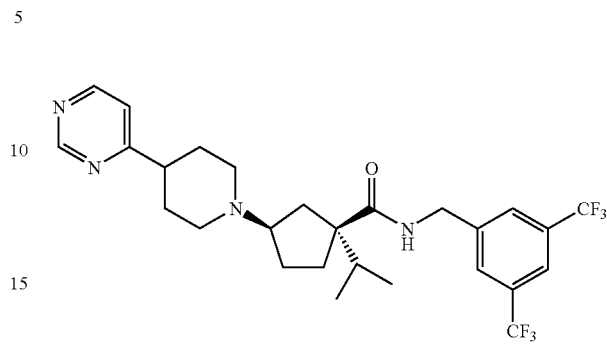

Step A

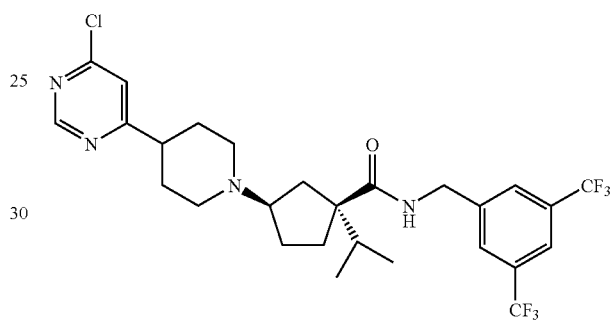

Ketone Intermediate 1 (100 mg, 0.253 mmol) was combined with 4-(6-chloro-4-pyrimidyl)-piperidine hydrochloride (prepared as described for Intermediate 5, 89 mg, 0.33 mmol), triethylamine (92 µL, 0.66 mmol), sodium triacetoxyborohydride (268 mg, 1.27 mmol) and 4° A molecular sieves (powder, 100 mg) in DCM (7 mL). After 2 days stirring at rt, the reaction was filtered and worked up as described in Example 1. Purification by preparative TLC (silica, 4% of 1:9 NH$_4$OH/methanol in DCM) afforded two bands corresponding to the cis (54.2 mg top spot) and trans isomers (25 mg bottom spot). Both the cis and trans isomers were converted to HCl salts by dissolving the free bases in ~1 mL of DCM, adding excess 1 N HCl in ether, and concentrating.

Top spot-ESI-MS calculated for C27H31ClF6N4O: 576; Found: 577 (M+H). Bottom spot-ESI-MS calculated for C27H31ClF6N4O: 576; Found: 577 (M+H).

Step B

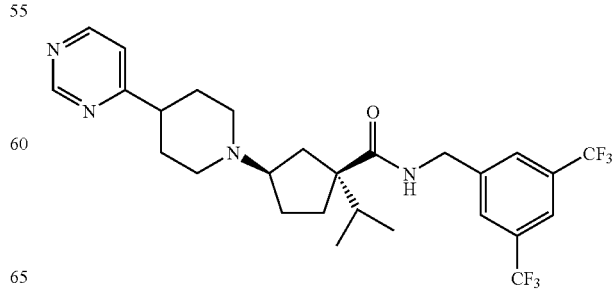

The free base of the cis-intermediate mixture from Step A (47.7 mg, 0.0827 mmol) was dissolved in 2 mL of ethyl acetate and sodium bicarbonate (10 mg) and 10% Pd/C (10 mg) were added. The reaction mixture was stirred under a hydrogen atmosphere (balloon) for 1.5 h. Since the reaction was proceeding slowly, more 10% Pd/C (10 mg) was added and the reaction mixture was stirred under a hydrogen atmosphere for an additional 1.5 h. The reaction mixture was filtered and concentrated, then resubmitted to the same conditions as above, this time directly using 20 mg of 10% Pd/C. After 5.5 h, the reaction was still incomplete and 2 mL methanol was added and the reaction was stirred under a hydrogen atmosphere for an additional 45 min, whereupon the reaction was observed to be complete. The reaction mixture was filtered through a 0.45 μm PTFE filter, then concentrated. Purification by preparative TLC (silica, 8% of 1:9 NH$_4$OH/methanol in DCM) afforded 44.5 mg of product as its free base. Conversion to the HCl salt was accomplished by dissolving the free base in 1 mL of DCM, adding excess of 1 N HCl in ether, then concentrating. ESI-MS calculated for C27H32F6N4O: 542; Found: 543 (M+H).

EXAMPLE 3

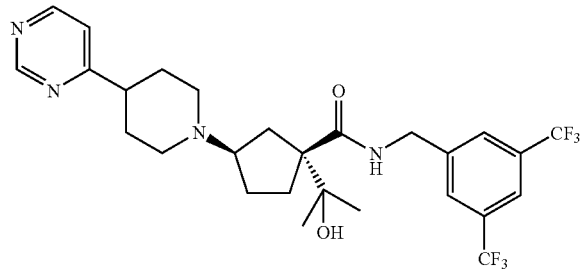

Ketone Intermediate 3 (200 mg, 0.487 mmol) was combined with 4-(5-pyrimidyl)-piperidine hydrochloride (prepared as described for Intermediate 5, 131 mg, 0.658 mmol), triethylamine (76 μL, 0.58 mmol), sodium triacetoxyborohydride (466 mg, 2.20 mmol) and 4° A molecular sieves (powder, 200 mg) in DCM (20 mL). The reaction mixture was stirred at rt for 2 days, then was filtered through a celite plug, and concentrated. Since the product had formed a stable boron complex, the residue was dissolved in 50 mL of 4:1 saturated aqueous NaHCO$_3$/methanol and warmed at 50° C. for 1-2 h. The mixture was extracted three times with DCM, and the combined organic layers were washed with brine, dried over anhydrous MgSO$_4$, filtered, and concentrated. Purification by preparative TLC (silica, 5% of 1:9 NH$_4$OH/methanol in DCM) afforded two bands corresponding to the cis (250 mg, top spot) and trans isomers (30 mg, bottom spot). Both trans isomers were converted to HCl salts by dissolving the free bases in ~1 mL of DCM, adding excess 1 N HCl in ether, and concentrating.

Top spot ESI-MS calculated for C27H32F6N4O2: 558; Found: 559 (M+H). Bottom spot-ESI-MS calculated for C27H32F6N4O2: 558; Found: 559 (M+H). Single cis-enantiomers were obtained via chiral HPLC, using Diacel's Chiralcel OD semipreparative column, eluting with 25% isopropyl alcohol/hexane (the free base was resolved) to give 69.7 mg of the lower Rf cis isomer and 76.8 mg of the higher Rf cis isomer. A variety of CCR-2 antagonists were prepared according to the same protocols as described for Examples 1-3 from intermediate ketones such as Intermediates 14 and amines such as Intermediates 5-30 as well as other known or commercially available amines. The Table below lists some of these analogs. Most were separated into two cis and two trans isomer sets, some were further resolved into single cis isomers by chiral HPLC.

TABLE

OTHER ANALOGS PREPARED SIMILARLY TO EXAMPLES 1-3

| Example | X | R$^1$ | R$^2$ | Calc. MW | Observed M + H by ESI-MS |
|---|---|---|---|---|---|
| 4 | ![triazole] | H | CF$_3$ | 531 | 532 |
| 5 | ![triazole] | H | CF$_3$ | 531 | 532 |
| 6 | ![triazole] | H | CF$_3$ | 531 | 532 |
| 7 | ![tetrazole] | H | CF$_3$ | 532 | 533 |
| 8 | ![tetrazole] | H | CF$_3$ | 532 | 533 |
| 9 | ![methyl-tetrazole] | H | CF$_3$ | 546 | 547 |
| 10 | ![imidazole] | H | CF$_3$ | 530 | 531 |
| 11 | ![pyrrole] | H | CF$_3$ | 529 | 530 |

TABLE-continued

OTHER ANALOGS PREPARED SIMILARLY TO EXAMPLES 1-3

| Example | X | R¹ | R² | Calc. MW | Observed M + H by ESI-MS |
|---|---|---|---|---|---|
| 12 | pyrazolyl | H | CF₃ | 530 | 531 |
| 13 | 1,2,4-triazol-4-yl | H | CF₃ | 531 | 532 |
| 14 | pyrazolyl | OH | CF₃ | 546 | 547 |
| 15 | imidazolyl | OH | CF₃ | 546 | 547 |
| 16 | 1,2,3-triazol-2-yl | OH | CF₃ | 547 | 548 |
| 17 | 1,2,3-triazol-1-yl | OH | CF₃ | 547 | 548 |
| 18 | 1,2,4-triazol-1-yl | OH | CF₃ | 547 | 548 |
| 19 | tetrazol-1-yl | OH | CF₃ | 548 | 549 |
| 20 | tetrazol-2-yl | OH | CF₃ | 548 | 549 |
| 21 | pyrazolyl | H | F | 480 | 481 |
| 22 | imidazolyl | H | F | 480 | 481 |
| 23 | 1,2,3-triazol-2-yl | H | F | 481 | 482 |
| 24 | 1,2,3-triazol-1-yl | H | F | 481 | 482 |
| 25 | 1,2,4-triazol-1-yl | H | F | 481 | 482 |
| 26 | tetrazol-1-yl | H | F | 482 | 483 |
| 27 | tetrazol-2-yl | H | F | 482 | 483 |
| 28 | indazolyl | H | CF₃ | 580 | 581 |

TABLE-continued
OTHER ANALOGS PREPARED SIMILARLY TO EXAMPLES 1-3
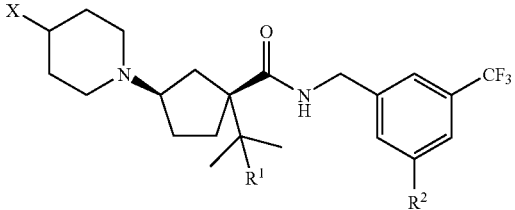
| Example | X | R¹ | R² | Calc. MW | Observed M + H by ESI-MS |
|---|---|---|---|---|---|
| 29 | 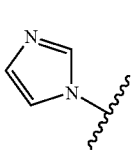 | OH | F | 496 | 497 |
| 30 | 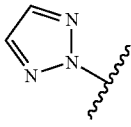 | OH | F | 496 | 497 |
| 31 | 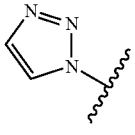 | OH | F | 497 | 498 |
| 32 | 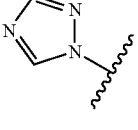 | OH | F | 497 | 498 |
| 33 | 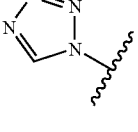 | OH | F | 497 | 498 |
| 34 | 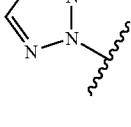 | OH | F | 498 | 499 |
| 35 | 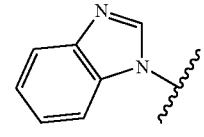 | OH | F | 498 | 499 |
| 36 | 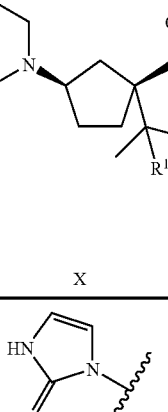 | H | CF₃ | 580 | 581 |
TABLE-continued
OTHER ANALOGS PREPARED SIMILARLY TO EXAMPLES 1-3
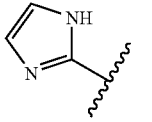
| Example | X | R¹ | R² | Calc. MW | Observed M + H by ESI-MS |
|---|---|---|---|---|---|
| 37 | 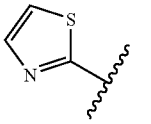 | H | CF₃ | 546 | 547 |
| 38 | 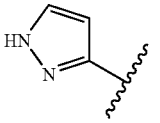 | H | CF₃ | 530 | 531 |
| 39 | 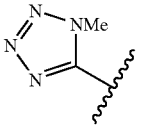 | H | CF₃ | 547 | 548 |
| 40 | 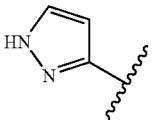 | H | CF₃ | 530 | 531 |
| 41 | 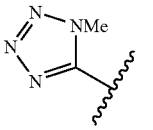 | OH | CF₃ | 562 | 563 |
| 42 | 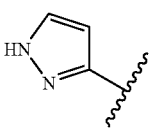 | H | F | 480 | 481 |
| 43 | 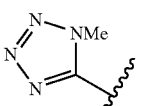 | H | F | 496 | 497 |
| 44 |  | OH | F | 496 | 497 |
| 45 |  | OH | F | 512 | 513 |

TABLE-continued

OTHER ANALOGS PREPARED SIMILARLY TO EXAMPLES 1-3

| Example | X | R¹ | R² | Calc. MW | Observed M + H by ESI-MS |
|---|---|---|---|---|---|
| 46 | pyrazine-2-yl | H | $CF_3$ | 542 | 543 |
| 47 | pyrimidin-2-yl | H | $CF_3$ | 542 | 543 |
| 48 | 6-chloropyridazin-3-yl | H | $CF_3$ | 577 | 578 |
| 49 | pyridazin-3-yl | H | $CF_3$ | 542 | 543 |
| 50 | 6-chloropyrimidin-4-yl | H | $CF_3$ | 577 | 578 |
| 51 | 2-aminothiazol-4-yl | H | $CF_3$ | 562 | 563 |
| 52 | 2-AcHN-thiazol-4-yl | H | $CF_3$ | 604 | 605 |
| 53 | 2-(MeOC(O)NH)-thiazol-4-yl | H | $CF_3$ | 620 | 621 |
| 54 | 2-(MsHN)-thiazol-4-yl | H | $CF_3$ | 640 | 641 |
| 55 | 5-oxo-1,2,4-thiadiazol-3-yl | H | $CF_3$ | 564 | 565 |
| 56 | pyrazol-4-yl | H | $CF_3$ | 530 | 531 |
| 57 | pyridin-3-yl | H | $CF_3$ | 541 | 542 |
| 58 | 2-AcNH-thiazol-5-yl | H | $CF_3$ | 604 | 605 |
| 59 | 2-(BnOC(O)NH)-thiazol-5-yl | H | $CF_3$ | 696 | 697 |
| 60 | 2-aminothiazol-5-yl | H | $CF_3$ | 562 | 563 |

TABLE-continued

OTHER ANALOGS PREPARED SIMILARLY TO EXAMPLES 1-3

| Example | X | R¹ | R² | Calc. MW | Observed M + H by ESI-MS |
|---|---|---|---|---|---|
| 61 | pyridazinyl | H | CF₃ | 542 | 543 |
| 62 | thiazolyl | H | CF₃ | 547 | 548 |

EXAMPLE 63

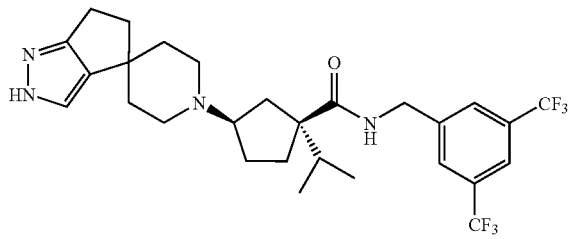

Example 63 was prepared in an identical fashion to Example 1 from Intermediate ketone 1 and the corresponding spiropiperidine. MW calc'd for C28H34F6N4O: 556; ESI-MS mass found: M+H=557.

EXAMPLE 64

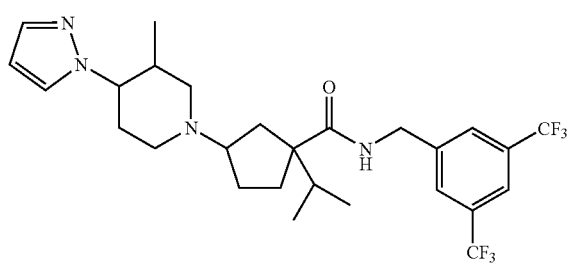

Step A:

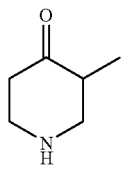

To a solution of N-benzyl-3-methyl-4-piperidone (25 g) in ethanol (200 mL) was added Pd/C (2 g). The mixture was agitated under H₂ (50 psi) on a Parr apparatus until H₂ uptake ceased. The catalyst was removed by filtration through celite and the filtrate was concentrated to give 14 g of crude product which was used without further purification.

Step B:

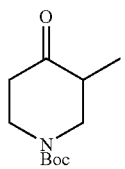

The crude product from Step A above (14 g, 0.124 mol) was dissolved in DCM (500 mL) and treated with di-tert-butyl dicarbonate (32 g, 0.15 mol). The reaction mixture was stirred at rt for 2 h then N,N-dimethylethylene diamine (2 mL) was added and the and the reaction mixture was stirred for another 30 min. The reaction mixture was washed with 5% citric acid, saturated NaHCO₃ solution and brine, dried over MgSO₄, filtered, and concentrated to give 20.7 g of desired product. ¹H NMR (500 MHz, CDCl₃): δ 4.18 (m, 2H), 3.22 (m, 1H), 2.80 (m, 1H), 2.55 (m, 1H), 2.42 (m, 2H), 1.47 (s, 9H), 1.02 (d, 3H).

Step C:

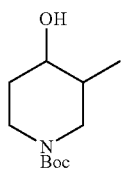

To a solution of the piperidine prepared as described in Step B (20.7 g, 97 mmol) in ethanol (200 mL) cooled in an ice bath was added portionwise sodium borohydride (4.41 g, 116 mmol). The reaction mixture was warmed to rt and stirred for 30 min. Water (50 mL) was added and after stirring for an additional 10 min, then reaction mixture was concentrated. The residue was partitioned between DCM and water, extracting 3 times with DCM. The combined organic layers were washed with water and brine, dried over anhydrous MgSO₄, filtered, and concentrated to give 21 g of alcohol product The H NMR spectrum was complex due to rotameric isomers and the presence of stereoisomers.

Step D:

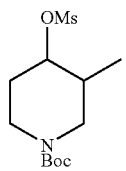

To an ice cold solution of the 4-piperidinol from Step C (6 g, 28 mmol) and triethylamine (5.1 mL, 37 mmol) in DCM (150 mL) was added dropwise methanesulfonyl chloride (2.4 mL, 31 mmol), and the resulting mixture was stirred at rt for 3 h. The reaction mixture was washed with water, 5% citric acid, saturated NaHCO$_3$ solution, and brine, dried over anhydrous MgSO$_4$, filtered, and concentrated to give 7.73 g of mesylate which was used directly in Step E.

Step E:

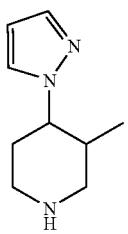

To a suspension of pyrazole (5.4 g, 79 mmol) in 100 mL of DMF under a nitrogen atmosphere was added portionwise sodium hydride (60% dispersion, 3.16 g, 79 mmol). After the addition was complete, the reaction mixture was stirred for an additional 15 min, then a solution of the piperidinol mesylate prepared as described in Steps A-D (7.73 g, 26 mmol) in 100 mL DMF was added by canula. The reaction mixture was stirred at rt for 2 days, then water was added and the mixture was extracted with ethyl acetate three times. The combined organic layers were washed three times with water, once with brine, dried over anhydrous MgSO$_4$, filtered, and concentrated.

The crude product was dissolved in methanol, saturated with HCl gas, and left standing overnight. The reaction mixture was concentrated and the residue was partitioned between saturated NaHCO$_3$ solution and DCM (extracted 3 times with DCM). The combined organic layers were dried over anhydrous Na$_2$SO$_4$, filtered, and concentrated. The residue was purified by flash chromatography (silica, 5-10% methanol/DCM+0.5% NH$_4$OH solution) to give 152 mg of product as a 3:2 mixture of isomers. $^1$H NMR (500 MHz, CDCl$_3$): δ 7.53 (d, J=1 Hz, 0.6H), 7.50 (d, J=2 Hz, 0.4H), 7.41 (d, J=3 Hz, 0.6), 7.40 (d, J=2 Hz, 0.4 H), 6.25 (m, 1H), 4.43 (dt, Jd=12 Hz, Jt=5 Hz, 0.61), 3.81 (m, 0.4H), 3.31 (dt, Jd=12 Hz, Jt=4 Hz, ~1H), 3.24-3.15 (m, ~0.75H), 2.97 (m, ~1.5H), 2.81-2.71 (m, ~1.25H), 2.39 (m, ~1.25 Hz), 2.19 (dd, J=11, 4 Hz, ~0.31), 2.14 (dd, J=11, 4 Hz, ~0.3H), 2.05-1.91 (m, ~2H), 0.74 (d, J=7 Hz, ~1.8H), 0.67 (d, J=6 Hz, ~1.2H).

Step F:

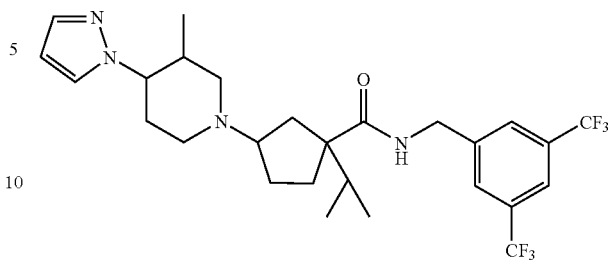

Reductive amination was accomplished in the usual way as shown in Example 1 starting from Intermediate ketone 1 (364 mg, 0.92 mmol) and the 4-pyrazolepiperidine prepared as described in Steps A-E above (152 mg, 0.92 mmol). Purification and separation of cis/trans isomers was accomplished by sequential preparative TLC plate elutions (0.5% NH$_4$OH solution/8% methanol/DCM then 0.5% NH$_4$OH solution/8% ethanol/ethyl acetate). Preparation of HCl salts was achieved by dissolving in MeOH and adding excess 4N HCl in dioxane, then concentrating to give 54 mg of the high band isomers (presumed mixture of 8 isomers) and 64 mg of the low band isomers (presumed mixture of 8 isomers).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of the formula I:

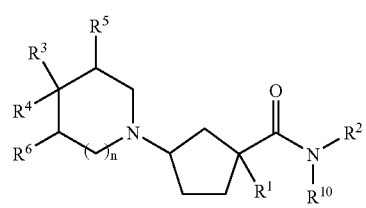

wherein:
R$^1$ is selected from the group consisting of:
(1) —CH(CH$_3$)$_2$ and
(2) —C(CH$_3$)$_2$(OH);
R$^2$ is selected from the group consisting of —CH$_2$-phenyl, —CH(CH$_3$)-phenyl, and —C(CH$_3$)$_2$-phenyl, wherein phenyl is unsubstituted or substituted with 1-3 substituents independently selected from:
(a) halo,
(b) trifluoromethyl,
(c) trifluoromethoxy,
(d) hydroxy,
(e) $C_{1-3}$alkyl,
(f) —O—$C_{1-3}$alkyl, and
(g) —$CO_2H$;
$R^3$ is a heterocycle, wherein the heterocycle is selected from the group consisting of benzoimidazolyl, imidazolyl, indazolyl, pyrazinyl, pyrazolyl, pyridazinyl, pyridyl, pyrimidyl, pyrrolyl, tetrazolyl, thiadiazolyl, thiazolyl, triazolyl, and imidazolidinone;
wherein the heterocycle is unsubstituted or substituted with 1-5 substituents independently selected from:
(a) halo,
(b) trifluoromethyl,
(c) hydroxy,
(d) $C_{1-3}$alkyl,
(e) —O—$C_{1-3}$alkyl,
(f) —$CO_2R^9$,
(g) —CN,
(h) —$NR^9R^{10}$, and
(i) —$CONR^9R^{10}$;
$R^4$, $R^6$, $R^9$ and $R^{10}$ are H;
$R^5$ is selected from:
(a) hydrogen,
(b) —$CH_3$, and
(c) —O—$CH_3$; and
n is the integer 1; or
a pharmaceutically acceptable salt thereof or an individual diastereomer thereof.

2. The compound of claim 1 wherein $R^2$ is selected from:
(1) —$CH_2$-(phenyl),
(2) —$CH_2$-(4-bromophenyl),
(3) —$CH_2$-(3-chlorophenyl),
(4) —$CH_2$-(3,5-difluorophenyl),
(5) —$CH_2$-((2-trifluoromethyl)phenyl),
(6) —$CH_2$-((3-trifluoromethyl)phenyl),
(7) —$CH_2$-((4-trifluoromethyl)phenyl),
(8) —$CH_2$-((3-trifluoromethoxy)phenyl),
(9) —$CH_2$-((3-trifluoromethoxy-5-methoxy)phenyl),
(10) —$CH_2$-((3,5-bis-trifluoromethyl)phenyl),
(11) —$CH_2$-((3-fluoro-5-trifluoromethyl)phenyl),
(12) —$CH(CH_3)$-((3,5-bis-trifluoromethyl)phenyl), and
(13) —$C(CH_3)_2$-((3,5-bis-trifluoromethyl)phenyl).

3. The compound of claim 1 wherein $R^3$ is heterocycle, where the heterocycle is selected from: imidazole, pyrimidyl, triazole and tetrazole,
where the heterocycle is unsubstituted or substituted with 1-5 substituents as defined in claim 1.

4. The compound of claim 1 wherein $R^3$ is heterocycle, where the heterocycle is unsubstituted or substituted with 1-3 substituents independently selected from:
(a) halo,
(c) hydroxy,
(d) $C_{1-3}$alkyl,
(e) —O—$C_{1-3}$alkyl, and
(f) —$CO_2R^9$.

5. The compound of claim 1 wherein $R^3$ is selected from: imidazole, pyrimidyl, triazole and tetrazole.

6. The compound of claim 1 wherein $R^3$ is selected from:

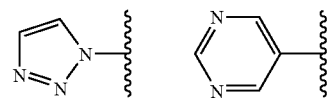

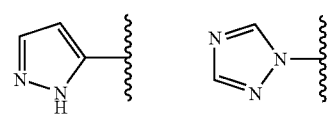

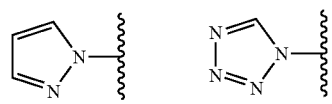

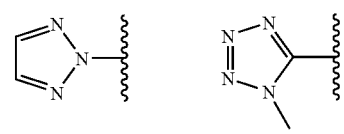

7. The compound of claim 1 which is selected from the group consisting of the compounds below, or a pharmaceutically acceptable salt or individual diastereomer thereof:

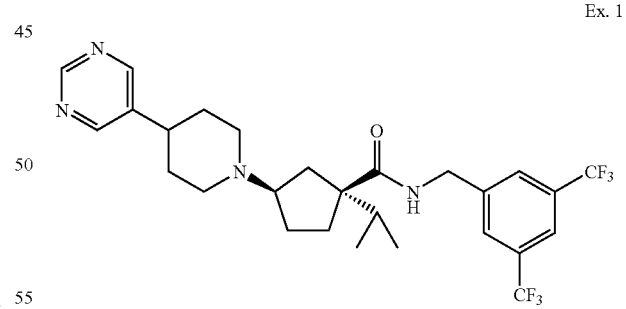

Ex. 1

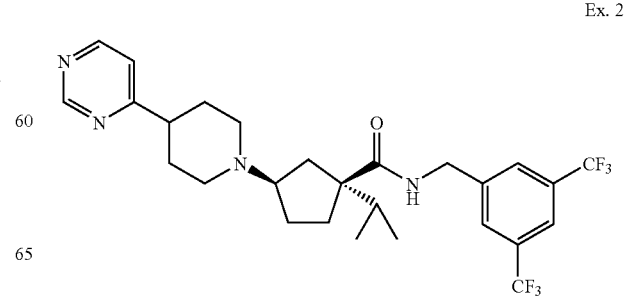

Ex. 2

-continued
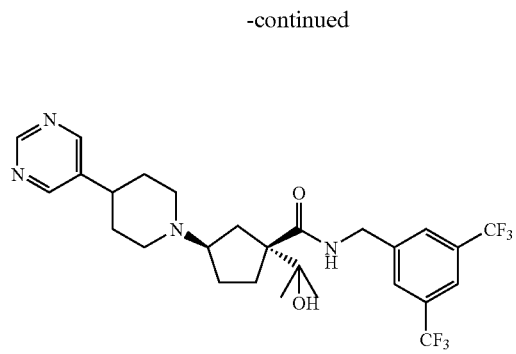
Ex. 3
and
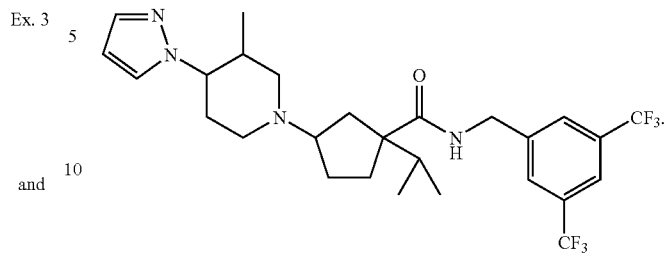
Ex. 64
8. A pharmaceutical composition which comprises an inert carrier and the compound of claim 1.
* * * * *